US010059015B2

(12) United States Patent
Schneider et al.

(10) Patent No.: US 10,059,015 B2
(45) Date of Patent: Aug. 28, 2018

(54) METHOD AND APPARATUS FOR POSITIONING A CUTTING APPARATUS

(71) Applicant: The Procter & Gamble Company, Cincinnati, OH (US)

(72) Inventors: Uwe Schneider, Cincinnati, OH (US); Daniel Patrick Findley, Finneytown, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 245 days.

(21) Appl. No.: 14/038,843

(22) Filed: Sep. 27, 2013

(65) Prior Publication Data
US 2014/0109739 A1 Apr. 24, 2014

Related U.S. Application Data

(60) Provisional application No. 61/717,285, filed on Oct. 23, 2012.

(51) Int. Cl.
*B26D 7/26* (2006.01)
*B26D 1/40* (2006.01)
(Continued)

(52) U.S. Cl.
CPC .............. *B26D 1/405* (2013.01); *A61F 13/00* (2013.01); *A61F 13/15723* (2013.01);
(Continued)

(58) Field of Classification Search
CPC .......... Y10T 83/4795; A61F 13/15723; A61F 13/15577; B26D 7/2628; B23D 35/008; B21B 31/10; B23Q 3/155–3/157
(Continued)

(56) References Cited

U.S. PATENT DOCUMENTS 3,675,456 A * 7/1972 Sieurin .................. B21B 31/10
72/239
3,951,268 A * 4/1976 Pell ........................ B21B 31/10
211/13.1
(Continued)

FOREIGN PATENT DOCUMENTS

EP 0 534 177 A1 3/1993
EP 1 798 011 A1 6/2007
(Continued)

OTHER PUBLICATIONS

PCT International Search Report PCT/US2003/065871, dated. Feb 12, 2014, 10 pages.

(Continued)

*Primary Examiner* — Kenneth E. Peterson
*Assistant Examiner* — Nhat Chieu Do
(74) *Attorney, Agent, or Firm* — Sarah M. DeCristofaro; Abbey A. Lopez

(57) ABSTRACT

A rotary cutting apparatus includes a frame movable in a first direction and a second direction that is opposite the first direction. The apparatus includes a cutting roll. The cutting roll is rotatably connected with the frame and configured to rotate about a first longitudinal axis. The apparatus includes an anvil roll. The anvil roll is rotatably connected with the frame and is configured to rotate about a second longitudinal axis. The first longitudinal axis is substantially parallel with the second longitudinal axis. The apparatus includes a first stationary member adapted to prevent movement of the frame in the first direction. The apparatus also includes a second stationary member connected with the frame. The second stationary member has a first configuration that prevents movement of the frame in the second direction. The second stationary member has a second configuration that allows movement of the frame in the second direction.

19 Claims, 18 Drawing Sheets

(51) Int. Cl.
  *B26D 5/00* (2006.01)
  *B26D 7/32* (2006.01)
  *A61F 13/15* (2006.01)
  *A61F 13/00* (2006.01)
  *B26F 1/38* (2006.01)

(52) U.S. Cl.
  CPC ............... *B26D 5/00* (2013.01); *B26D 7/26* (2013.01); *B26D 7/2628* (2013.01); *B26D 7/32* (2013.01); *B26D 7/265* (2013.01); *B26F 1/384* (2013.01); *Y10T 29/49778* (2015.01); *Y10T 83/0467* (2015.04); *Y10T 83/4795* (2015.04); *Y10T 83/4838* (2015.04)

(58) Field of Classification Search
  USPC .......... 83/304–305, 346, 563–564, 358–359, 83/58–68; 72/239
  See application file for complete search history.

(56) References Cited

U.S. PATENT DOCUMENTS

| | | | |
|---|---|---|---|
| 3,953,956 A * | 5/1976 | Massman | B65B 7/20 493/60 |
| 4,327,620 A * | 5/1982 | Greinke | B23D 35/008 83/479 |
| 4,905,493 A * | 3/1990 | Benedetti | B21B 13/001 72/225 |
| 5,207,138 A | 5/1993 | Sato et al. | |
| 5,350,348 A * | 9/1994 | Guot | B31B 1/00 493/324 |
| 5,715,720 A * | 2/1998 | Balve | B21B 13/02 72/237 |
| 6,418,827 B1 | 7/2002 | Bussey, III et al. | |
| 6,425,278 B1 * | 7/2002 | Aratani | B21B 31/103 72/239 |
| 7,569,039 B2 | 8/2009 | Matsuda et al. | |
| 2003/0035143 A1 | 2/2003 | Glemser et al. | |
| 2003/0172785 A1 * | 9/2003 | Formon | B26D 5/00 83/37 |
| 2005/0103173 A1 * | 5/2005 | Elkis | B23D 35/008 83/343 |
| 2005/0107764 A1 | 5/2005 | Matsuda et al. | |
| 2007/0219521 A1 | 9/2007 | Hird et al. | |
| 2011/0139657 A1 | 6/2011 | Hird et al. | |
| 2011/0139658 A1 | 6/2011 | Hird et al. | |
| 2011/0139659 A1 | 6/2011 | Hird et al. | |
| 2011/0139662 A1 | 6/2011 | Hird et al. | |
| 2011/0152812 A1 | 6/2011 | Hird et al. | |
| 2012/0061015 A1 | 3/2012 | LaVon et al. | |
| 2012/0061016 A1 | 3/2012 | LaVon et al. | |
| 2012/0255411 A1 * | 10/2012 | Dijon | B26D 7/265 83/344 |

FOREIGN PATENT DOCUMENTS

| | | |
|---|---|---|
| GB | 2 458 686 A1 | 9/2009 |
| JP | 62-188697 | 8/1987 |
| JP | 2003-20635 U | 1/2003 |
| JP | 2005-340773 A | 12/2005 |

OTHER PUBLICATIONS

PCT International Search Report PCT/US2003/066000, dated Feb. 12, 2014, 9 pages.

* cited by examiner

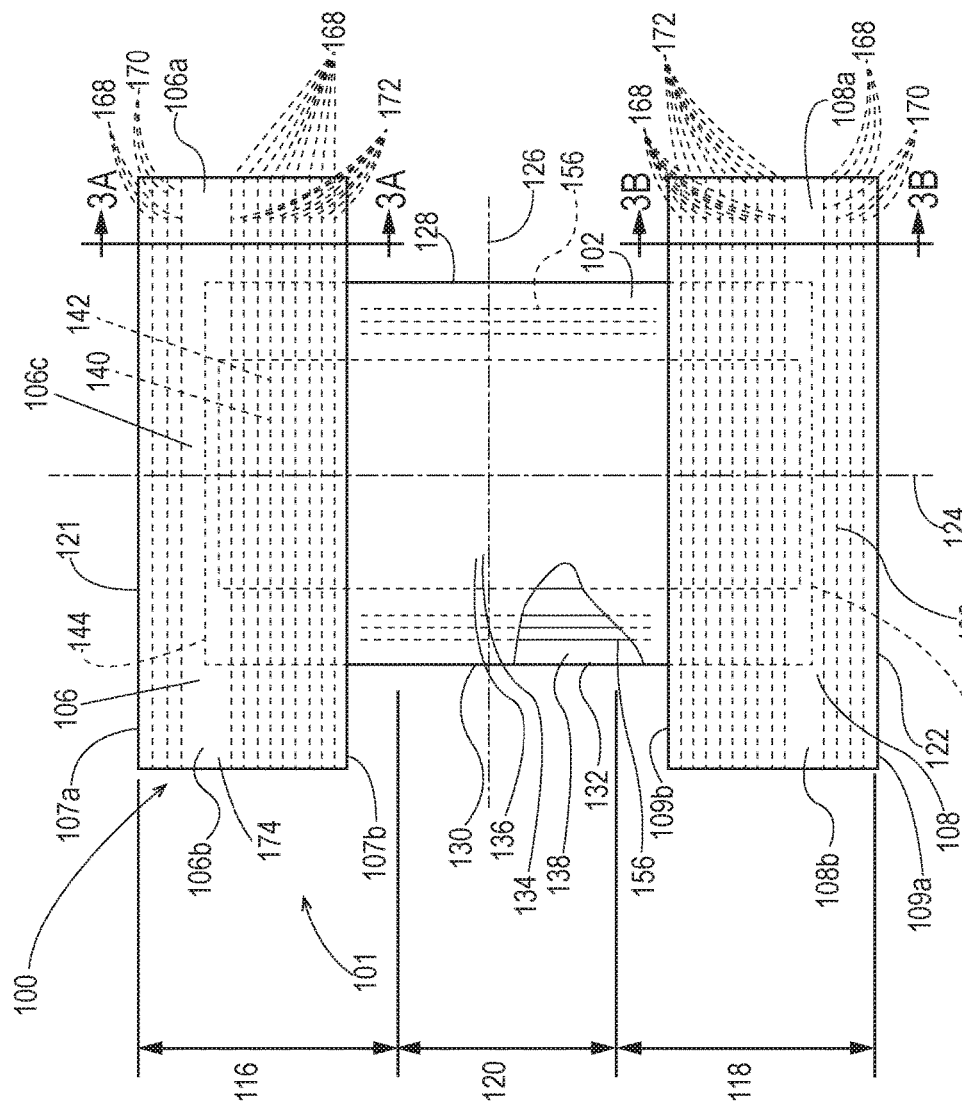

METHOD AND APPARATUS FOR POSITIONING A CUTTING APPARATUS

CROSS-REFERENCE TO RELATED APPLICATIONS

This application claims the benefit of U.S. Provisional Application Ser. No. 61/717,285, filed Oct. 23, 2012, the entirety of which is incorporated by reference herein.

FIELD OF THE INVENTION

The present disclosure relates to methods and apparatuses for manufacturing absorbent articles, and more particularly, to methods and apparatuses for positioning a cutting apparatus during the manufacture of absorbent articles.

BACKGROUND OF THE INVENTION

Along an assembly line, various types of articles, such as diapers and other absorbent articles, may be assembled by adding components to and/or otherwise modifying an advancing, continuous web of material. For example, in some processes, advancing webs of material are combined with other advancing webs of material. In other examples, individual components created from advancing webs of material are combined with advancing webs of material, which in turn, are then combined with other advancing webs of material. In some cases, individual components created from advancing webs are combined with other individual components created from other advancing webs. Webs of material and component parts used to manufacture diapers may include: backsheets, topsheets, leg cuffs, waist bands, absorbent core components, front and/or back ears, fastening components, and various types of elastic webs and components such as leg elastics, barrier leg cuff elastics, stretch side panels, and waist elastics. Once the desired component parts are assembled, the advancing webs and component parts are subjected to a final cut to separate the webs into discrete diapers or other absorbent articles.

In some processes, a continuous length of diaper chassis advancing in a machine direction is cut into discrete chassis and combined with continuous lengths of elastically extendable front and back waistband webs advancing in the machine direction. In some cutting processes, the continuous length of chassis is advanced onto a rotating cutting roll and cut into discrete chassis. In some processes, the discrete chassis may be transferred from the cutting roll to a transfer apparatus. The transfer apparatus may reorient the discrete chassis prior to joining the discrete chassis with the continuous lengths of first and second waistband webs. The transfer apparatus may be located adjacent to the cutting roll so as to form a gap there between.

Various defective operating conditions may cause the continuous length of chassis web to be incompletely cut by the cutting roll. For example, the cutting roll may become dull, the chassis web may slip, or the chassis web may stick to the cutting roll during the cutting process. As such, the continuous length of chassis web may fail to transfer to the transfer apparatus, and, instead, may wrap around the cutting roll. As the continuous length of chassis web wraps around the cutting roll, the continuous length of chassis web expands radially around the cutting roll and fills the gap between the cutting roll and the transfer apparatus. The radially expanding wrapped chassis may undesirably contact and apply reactive forces to the transfer apparatus and the cutting roll. Consequently, if the converting apparatus is not promptly shut down, the cutting roll and/or adjacent equipment may be damaged.

Thus, it would be beneficial to provide a process and apparatus for preventing damage to a cutting roll and/or adjacent equipment if a defective operating condition occurs during a cutting process.

SUMMARY OF THE INVENTION

Aspects of the present disclosure include a rotary cutting apparatus. The rotary cutting apparatus comprises a frame movable in a first direction and a second direction, wherein the first direction is opposite the second direction. The rotary cutting apparatus comprises a cutting roll defining a first longitudinal axis, wherein the cutting roll is rotatably connected with the frame and configured to rotate about the first longitudinal axis. The rotary cutting apparatus comprises an anvil roll defining a second longitudinal axis, wherein the anvil roll is rotatably connected with the frame and configured to rotate about the second longitudinal axis. The anvil roll is positioned relative to the cutting roll such that the first longitudinal axis is substantially parallel with the second longitudinal axis. The rotary cutting apparatus comprises a first blocking member adapted to prevent movement of the frame in the first direction. The rotary cutting apparatus comprises a second blocking member connected with the frame. The second blocking member has first and second configurations. In the first configuration, the second blocking member prevents movement of the frame in the second direction. In the second configuration, the second blocking member allows movement of the frame in the second direction.

Aspects of the present disclosure include a rotary cutting apparatus having a first mode of operation and a second mode of operation. The rotary cutting apparatus comprises a frame movable in a first direction and a second direction, wherein the first direction is opposite the second direction. The rotary cutting apparatus comprises a cutting roll rotatably connected with the frame. The rotary cutting apparatus comprises a first blocking member located adjacent to the frame and a second blocking member connected with the frame. In the first mode of operation, the first blocking member prevents movement of the frame in the first direction and the second blocking member prevents movement of the frame in the second direction. In the second mode of operation, the second blocking member allows movement of the frame in the second direction.

In other aspects, the present disclosure includes a method for positioning a cutting apparatus. The cutting apparatus comprises a frame. The frame is movable in a first direction and a second direction, wherein the first direction is opposite the second direction. The cutting apparatus comprises a cutting roll rotatably connected with the frame and an anvil roll rotatably connected with the frame. The cutting apparatus comprises a first blocking member that is adapted to prevent movement of the frame in the first direction. The cutting apparatus comprises a second blocking member that is connected with the frame. The second blocking member has a first configuration that prevents movement of the frame in the second direction and a second configuration that allows movement of the frame in the second direction. The method comprises the steps of: setting the second blocking member in the first configuration; advancing a continuous substrate in a machine direction between the cutting roll and the anvil roll; sensing a defective operating condition wherein the continuous substrate is advancing between the cutting roll and the anvil without being cut; and switching the second blocking member to the second configuration upon sensing the defective operating condition; and moving the frame in the second direction.

BRIEF DESCRIPTION OF THE DRAWINGS

FIG. 2A is a partially cut-away, plan view of a diaper pant.

DETAILED DESCRIPTION OF THE INVENTION

Figure 1:
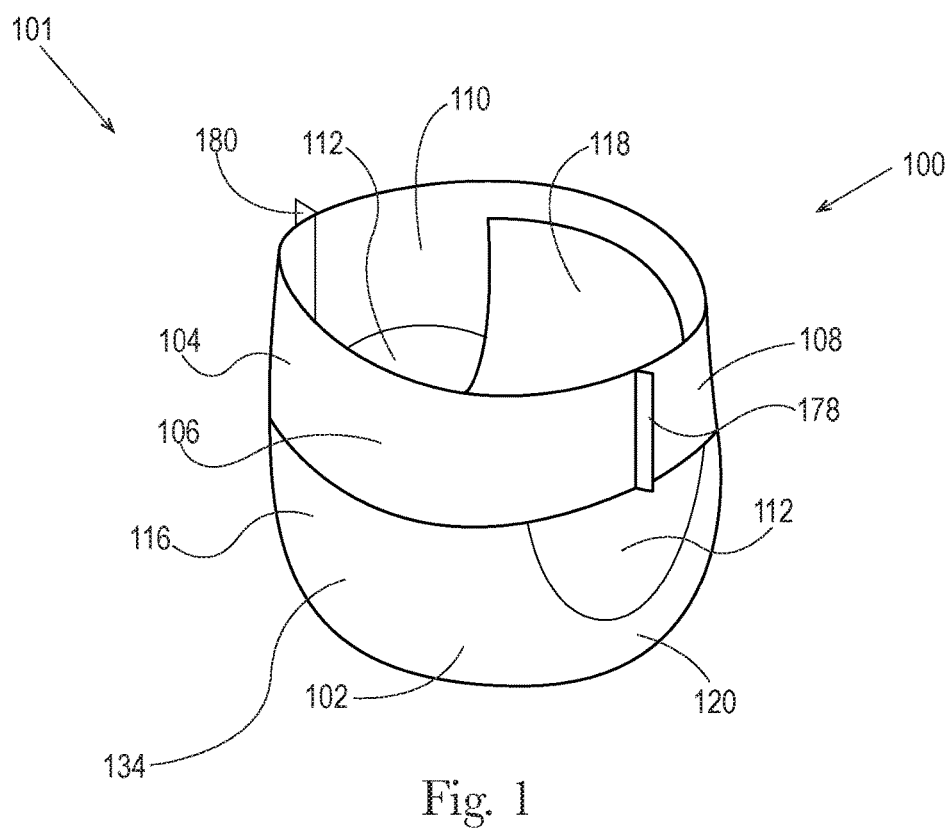
FIG. 1 is a schematic, perspective view of a diaper pant.

The following definitions may be useful in understanding the present disclosure:

"Absorbent article" is used herein to refer to consumer products whose primary function is to absorb and retain soils and wastes. "Diaper" is used herein to refer to an absorbent article generally worn by infants and incontinent persons about the lower torso. The term "disposable" is used herein to describe absorbent articles which generally are not intended to be laundered or otherwise restored or reused as an absorbent article (e.g., they are intended to be discarded after a single use and may also be configured to be recycled, composted or otherwise disposed of in an environmentally compatible manner).

"Longitudinal" means a direction running substantially perpendicular from a waist edge to a longitudinally opposing waist edge of an absorbent article when the article is in a flat out, uncontracted state, or from a waist edge to the bottom of the crotch, i.e. the fold line, in a bi-folded article. Directions within 45 degrees of the longitudinal direction are considered to be "longitudinal." "Lateral" refers to a direction running from a longitudinally extending side edge to a laterally opposing longitudinally extending side edge of an article and generally at a right angle to the longitudinal direction. Directions within 45 degrees of the lateral direction are considered to be "lateral."

"Substrate" refers herein to a material that is primarily two-dimensional (i.e. in an XY plane) and whose thickness (in a Z direction) is relatively small (i.e. 1/10 or less) in comparison to the substrate's length (in an X direction) and width (in a Y direction). Non-limiting examples of substrates include a web, layer or layers or fibrous materials, nonwovens, films and foils such as polymeric films or metallic foils. These materials may be used alone or may comprise two or more layers. As such, a web is a substrate.

"Machine direction" (MD) refers herein to the direction of material flow through a process. In addition, relative placement and movement of material can be described as flowing in the machine direction through a process from upstream in the process to downstream in the process.

"Cross direction" (CD) refers herein to a direction that is not parallel with, and usually perpendicular to, the machine direction.

"Pant" (also referred to as "training pant", "pre-closed diaper", "diaper pant", "pant diaper", and "pull-on diaper") refers herein to disposable absorbent articles having a continuous perimeter waist opening and continuous perimeter leg openings designed for infant or adult wearers. A pant can be configured with a continuous or closed waist opening and at least one continuous, closed, leg opening prior to the article being applied to the wearer. A pant can be preformed by various techniques including, but not limited to, joining together portions of the article using any refastenable and/or permanent closure member (e.g., seams, heat bonds, pressure welds, adhesives, cohesive bonds, mechanical fasteners, etc.). A pant can be preformed anywhere along the circumference of the article in the waist region (e.g., side fastened or seamed, front waist fastened or seamed, rear waist fastened or seamed).

"Pre-fastened" refers herein to pant diapers manufactured and provided to consumers in a configuration wherein the front waist region and the back waist region are fastened or connected to each other as packaged, prior to being applied to the wearer. As such pant diapers may have a continuous perimeter waist opening and continuous perimeter leg openings designed for infant or adult wearers. Pant diapers can be preformed anywhere along the circumference of the waist region (e.g., side fastened or connected, front waist fastened or connected, rear waist fastened or connected).

Aspects of the present disclosure involve methods and apparatuses for manufacturing absorbent articles, and more particularly, methods and apparatuses for controlling the position of a rotary cutting apparatus during the manufacture of absorbent articles. As discussed in more detail below, the rotary cutting apparatus may be configured in a first mode of operation, referred to herein as an operating configuration, and in a second mode of operation, referred to herein as a fail-safe configuration. In the operating configuration, the rotary cutting apparatus may be configured to cut a continuous length of chassis assemblies into discrete chassis. The rotary cutting apparatus may be configured with a sensor to detect a defective operation condition, such as a continuous web wrapping around the cutting roll. If the sensor detects a defective operating condition, the rotary cutting apparatus is configured to switch from the operating configuration to the fail-safe configuration in order to prevent damage to the rotary cutting apparatus and/or adjacent equipment.

A rotary cutting apparatus may comprise a frame that is movable in a first direction and a second direction, wherein the first direction is opposite the second direction. The rotary cutting apparatus may also include a track. The frame is moveably connected with the track. In some instances, the frame may be slideably connected with the track. The rotary cutting apparatus includes a cutting roll defining a first longitudinal axis. The cutting roll is rotatably connected with the frame and configured to rotate about the first longitudinal axis. The rotary cutting apparatus also includes an anvil roll defining a second longitudinal axis. The anvil roll is rotatably connected with the frame and configured to rotate about the second longitudinal axis. The anvil roll is positioned relative to the cutting roll such that the first longitudinal axis is substantially parallel with the second longitudinal axis. The rotary cutting apparatus includes a first blocking member adapted to prevent movement of the frame in the first direction. The rotary cutting apparatus includes a second blocking member connected with the frame. The second blocking member has a first configuration and a second configuration. In the first configuration, the second blocking member prevents movement of the frame in the second direction. Also, in the first configuration, the second blocking member may be adapted to apply a positive force to the frame in the first direction. In the second configuration, the second blocking member allows movement of the frame in the second direction. In some exemplary configurations, the first longitudinal axis is orthogonal to the first and second directions. The rotary cutting apparatus further comprises a sensor that is adapted to detect a defective operating condition. If the sensor detects a defecting operating condition, the second blocking member shifts from the first configuration to the second configuration.

With the rotary cutting apparatus in an operating configuration, the second blocking member is set in the first configuration. In operation, a continuous substrate advances in a machine direction between the cutting roll and the anvil roll to be cut into discrete components. If the sensor detects a defective operating condition, the rotary cutting apparatus switches from the operating configuration to the fail-safe configuration and the second blocking member switches from the first configuration to the second configuration. As a result, the frame is able to move in the second direction as the continuous length of chassis assemblies wrap around the cutting roll.

While the apparatuses and methods of the present disclosure are discussed in the context of cutting continuous lengths of chassis assemblies that may be used in the assembly of pant diapers, it is to be appreciated that the rotary cutting apparatus of the present disclosure may be used to cut substrates into various components that may be used in the manufacture of absorbent articles.

As previously mentioned, the methods and apparatuses discussed herein may be used to manufacture absorbent articles. To help provide additional context to the subsequent discussion, the following provides a general description of absorbent articles in the form of diaper pants that may be manufactured in accordance with the methods and apparatuses disclosed herein. While the present disclosure relates to cutting continuous lengths of chassis assemblies for diaper pants, it is to be appreciated that the methods and apparatuses disclosed herein may be used with various types of absorbent articles.

FIGS. 1 and 2A show an exemplary absorbent article 100 in the form of a diaper pant 101 that may be formed in accordance with the apparatuses and methods disclosed herein. In particular, FIG. 1 is a perspective view of a diaper pant 101 in a pre-fastened configuration and FIG. 2A shows a plan view of the diaper pant 101 with the portion of the diaper pant 101 that faces away from a wearer oriented toward the viewer. The diaper pant 101 shown in FIGS. 1 and 2A includes a chassis 102 and a ring-like elastic belt 104. As discussed below in more detail, A first elastic belt 106 and a second elastic belt 108 are connected together to form the ring-like elastic belt 104.

With continued reference to FIG. 2A, the chassis 102 includes a first waist region 116, a second waist region 118, and a crotch region 120 disposed intermediate the first and second waist regions 116 and 118. The first waist region 116 may be configured as a front waist region, and the second waist region 118 may be configured as back waist region. In some embodiments, the length of each of the front waist region 116, back waist region 118, and crotch region 120 may be one-third of the length of the absorbent article 100. The diaper pant 101 may also include a laterally extending front waist edge 121 in the front waist region 116 and a longitudinally opposing and laterally extending back waist edge 122 in the back waist region 118. To provide a frame of reference for the present discussion, the diaper pant 101 and chassis 102 of FIG. 2A are shown with a longitudinal axis 124 and a lateral axis 126. In some embodiments, the longitudinal axis 124 may extend through the front waist edge 121 and through the back waist edge 122. The lateral axis 126 may extend through a first longitudinal or right side edge 128 and through a midpoint of a second longitudinal or left side edge 130 of the chassis 102.

As shown in FIGS. 1 and 2A, the diaper pant 101 may include an inner, body facing surface 132, and an outer, garment facing surface 134. The chassis 102 may include a backsheet 136 and a topsheet 138. The chassis 102 may also include an absorbent assembly 140, including an absorbent core 142, disposed between a portion of the topsheet 138 and the backsheet 136. As discussed in more detail below, the diaper pant 101 may also include other features, such as leg elastics 156 and/or leg cuffs to enhance the fit around the legs of the wearer.

As shown in FIG. 2A, the periphery of the chassis 102 may be defined by the first longitudinal side edge 128, a second longitudinal side edge 130, a first laterally extending end edge 144 disposed in the first waist region 116, and a second laterally extending end edge 146 disposed in the second waist region 118. Both side edges 128 and 130 extend longitudinally between the first end edge 144 and the second end edge 146. As shown in FIG. 2A, the laterally extending end edges 144 and 146 are located longitudinally inward from the laterally extending front waist edge 121 in the front waist region 116 and the laterally extending back waist edge 122 in the back waist region 118. When the diaper pant 101 is worn on the lower torso of a wearer, the front waist edge 121 and the back waist edge 122 of the chassis 102 may encircle a portion of the waist of the wearer. At the same time, the chassis side edges 128 and 130 may encircle at least a portion of the legs of the wearer. And the crotch region 120 may be generally positioned between the legs of the wearer with the absorbent core 142 extending from the front waist region 116 through the crotch region 120 to the back waist region 118.

Referring to FIG. 2A, the diaper pant 101 may also include elasticized leg cuffs 156. It is to be appreciated that the leg cuffs 156 can be and are sometimes also referred to as leg bands, side flaps, barrier cuffs, elastic cuffs or gasketing cuffs. The elasticized leg cuffs 156 may be configured in various ways to help reduce the leakage of body exudates in the leg regions.

Diaper pants may be manufactured with a ring-like elastic belt 104 and provided to consumers in a configuration wherein the front waist region 116 and the back waist region 118 are connected to each other as packaged, prior to being applied to the wearer. As such, diaper pants 101 may have a continuous perimeter waist opening 110 and continuous perimeter leg openings 112 such as shown in FIG. 1. The ring-like elastic belt 104 is defined by a first elastic belt 106 connected with a second elastic belt 108. As shown in FIG. 2A, the first elastic belt 106 defines first and second opposing end regions 106a, 106b and a central region 106c, and the second elastic 108 belt defines first and second opposing end regions 108a, 108b and a central region 108c. The central region 106c of the first elastic belt 106 is connected with the first waist region 116 of the chassis 102, and the central region 108c of the second elastic belt 108 is connected with the second waist region 118 of the chassis 102. FIGS. 1 and 2A, the first end region 106a of the first elastic belt 106 is connected with the first end region 108a of the second elastic belt 108 at first side seam 178, and the second end region 106b of the first elastic belt 106 is connected with the second end region 108b of the second elastic belt 108 at second side seam 180 to define the ring-like elastic belt 104 as well as the waist opening 110 and leg openings 112.

Figure 2B:
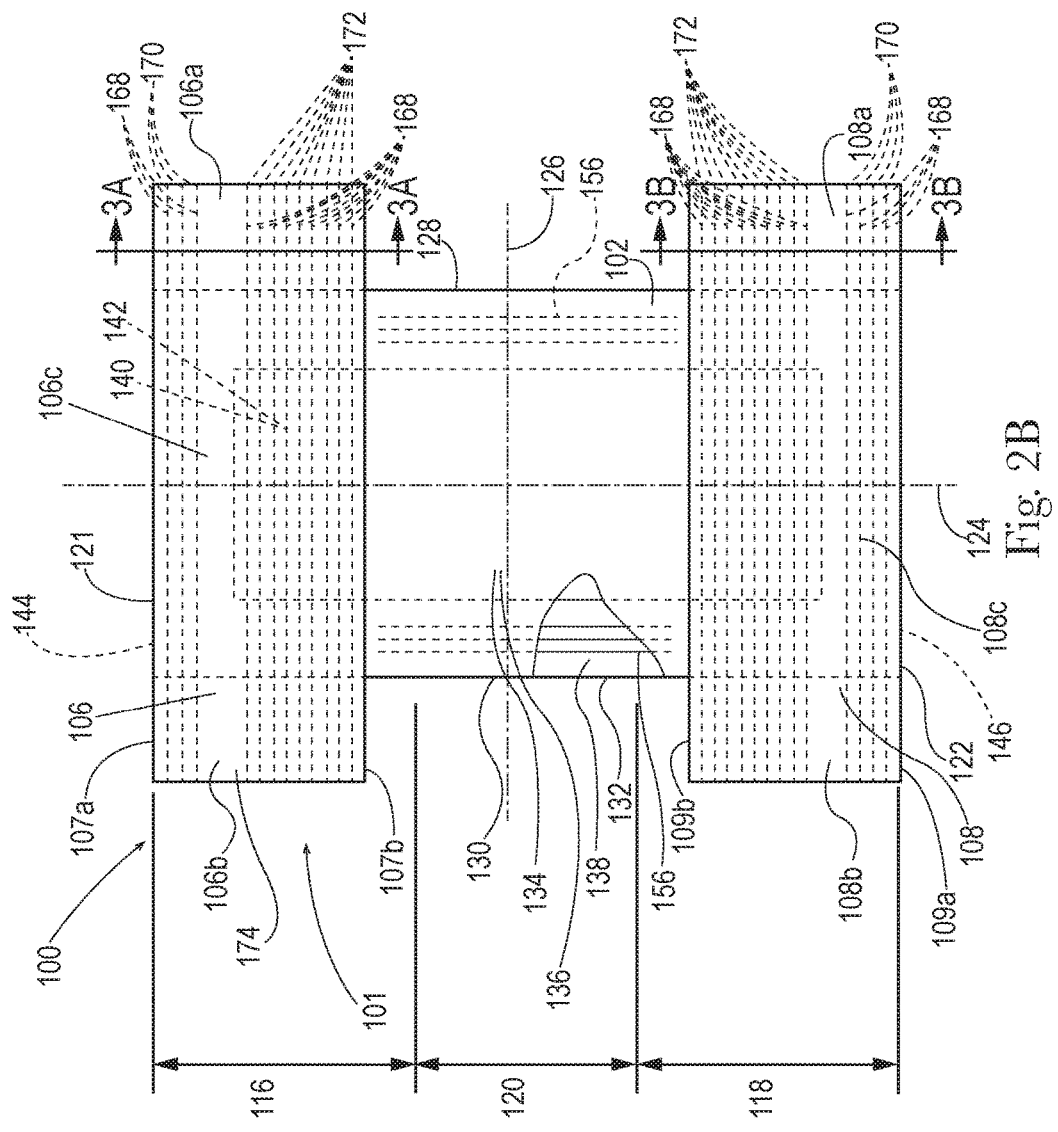
FIG. 2B is a partially cut-away, plan view of a diaper pant.
Figure 3A:
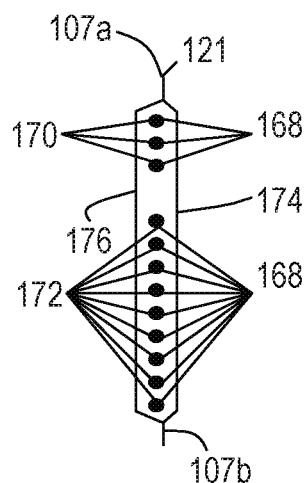
FIG. 3A is a cross-sectional view of the diaper pant of FIGS. 2A and 2B taken along line 3A-3A.
Figure 3B:
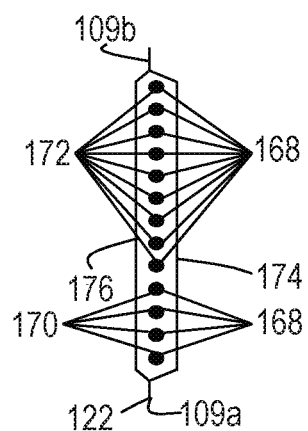
FIG. 3B is a cross-sectional view of the diaper pant of FIGS. 2A and 2B taken along line 3B-3B.

Referring to FIGS. 2A, 3A, and 3B, the first elastic belt 106 also defines an outer lateral edge 107a and an inner lateral edge 107b, and the second elastic belt 108 defines an outer lateral edge 109a and an inner lateral edge 109b. The outer lateral edges 107a, 109a may also define the front waist edge 121 and the laterally extending back waist edge 122. The first elastic belt 106 and the second elastic belt 108 may also each include an outer, garment facing layer 174 and an inner, wearer facing layer 176. It is to be appreciated that the first elastic belt 106 and the second elastic belt 108 may comprise the same materials and/or may have the same structure. In some embodiments, the first elastic belt 106 and the second elastic belt may comprise different materials and/or may have different structures. It should also be appreciated that the first elastic belt 106 and the second elastic belt 108 may be constructed from various materials. For example, the first and second belts may be manufactured from materials such as plastic films; apertured plastic films; woven or nonwoven webs of natural materials (e.g., wood or cotton fibers), synthetic fibers (e.g., polyolefins, polyamides, polyester, polyethylene, or polypropylene fibers) or a combination of natural and/or synthetic fibers; or coated woven or nonwoven webs. In some embodiments, the first and second elastic belts include a nonwoven web of synthetic fibers, and may include a stretchable nonwoven. In other embodiments, the first and second elastic belts include an inner hydrophobic, non-stretchable nonwoven material and an outer hydrophobic, non-stretchable nonwoven material.

The first and second elastic belts 106, 108 may also each include belt elastic material interposed between the outer layer 174 and the inner layer 176. The belt elastic material may include one or more elastic elements such as strands, ribbons, or panels extending along the lengths of the elastic belts. As shown in FIGS. 2A, 3A, and 3B, the belt elastic material may include a plurality of elastic strands 168, which may be referred to herein as outer, waist elastics 170 and inner, waist elastics 172. As shown in FIG. 2A, the elastic strands 168 continuously extend laterally between the first and second opposing end regions 106a, 106b of the first elastic belt 106 and between the first and second opposing end regions 108a, 108b of the second elastic belt 108. In some embodiments, some elastic strands 168 may be configured with discontinuities in areas, such as for example, where the first and second elastic belts 106, 108 overlap the absorbent assembly 140. In some embodiments, the elastic strands 168 may be disposed at a constant interval in the longitudinal direction. In other embodiments, the elastic strands 168 may be disposed at different intervals in the longitudinal direction. The belt elastic material in a stretched condition may be interposed and joined between the uncontracted outer layer 174 and the uncontracted inner layer 176. When the belt elastic material is relaxed, the belt elastic material returns to an unstretched condition and contracts the outer layer 174 and the inner layer 176. The belt elastic material may provide a desired variation of contraction force in the area of the ring-like elastic belt.

It is to be appreciated that the chassis 102 and elastic belts 106, 108 may be configured in different ways other than as depicted in FIG. 2A. For example, FIG. 2B shows a plan view of a diaper pant 101 having the same components as described above with reference to FIG. 2A, except the first laterally extending end edge 144 of the chassis 102 is aligned along and coincides with the front waist edge 121 of the pant 101, and the second laterally extending end edge 146 is aligned along and coincides with the back waist edge 122 of the pant 101.

Components of the disposable absorbent article (i.e., diaper, disposable pant, adult incontinence article, sanitary napkin, pantiliner, etc.) described in this specification can at least partially be comprised of bio-sourced content as described in US 2007/0219521A1 Hird et al published on Sep. 20, 2007, US 2011/0139658A1 Hird et al published on Jun. 16, 2011, US 2011/0139657A1 Hird et al published on Jun. 16, 2011, US 2011/0152812A1 Hird et al published on Jun. 23, 2011, US 2011/0139662A1 Hird et al published on Jun. 16, 2011, and US 2011/0139659A1 Hird et al published on Jun. 16, 2011. These components include, but are not limited to, topsheet nonwovens, backsheet films, backsheet nonwovens, side panel nonwovens, barrier leg cuff nonwovens, super absorbent, nonwoven acquisition layers, core wrap nonwovens, adhesives, fastener hooks, and fastener landing zone nonwovens and film bases.

In at least one exemplary configuration, a disposable absorbent article component comprises a bio-based content value from about 10% to about 100% using ASTM D6866-10, method B, in another embodiment, from about 25% to about 75%, and in yet another embodiment, from about 50% to about 60% using ASTM D6866-10, method B.

In order to apply the methodology of ASTM D6866-10 to determine the bio-based content of any disposable absorbent article component, a representative sample of the disposable absorbent article component must be obtained for testing. In at least one embodiment, the disposable absorbent article component can be ground into particulates less than about 20 mesh using known grinding methods (e.g., Wiley® mill), and a representative sample of suitable mass taken from the randomly mixed particles.

Figure 4A:
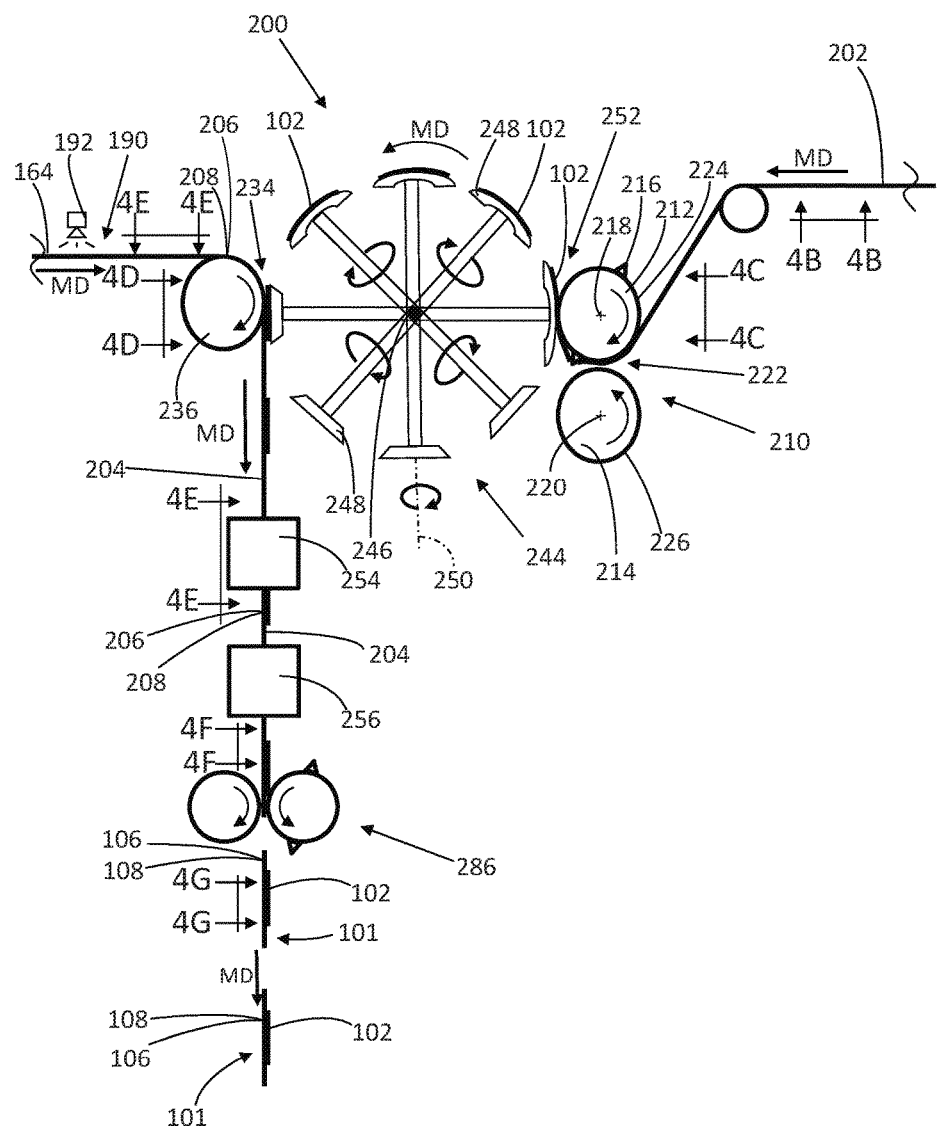
FIG. 4A is a schematic, side elevation view of a converting apparatus.

As previously discussed, the apparatuses and methods of the present disclosure may be utilized to assemble various components of pre-fastened diaper pants 101. For example, FIG. 4A shows a schematic view of a converting apparatus 200 adapted to manufacture diaper pants 101. The method of operation of the converting apparatus 200 may be described with reference to the various components of diaper pant 101 described above and shown in FIGS. 1 and 2A. Although the following methods are provided in the context of the diaper pants 101 shown in FIGS. 1 and 2A, it is to be appreciated that various embodiments of diaper pants can be manufactured according the methods disclosed herein, such as for example, the absorbent articles disclosed in U.S. Pat. No. 7,569,039, filed on Nov. 10, 2004; U.S. Patent Publication No. 2005/0107764, published May 19, 2005; U.S. Patent Application No. 2012/0061016, published Mar. 15, 2012; and U.S. Patent Publication No. 2012/0061015, published Mar. 15, 2012.

With reference to FIG. 4A, and as discussed in more detail below, in an operating configuration, a converting apparatus 200 operates to advance a continuous length of chassis assemblies 202 along a machine direction MD such that the longitudinal axis is parallel with the machine direction MD. The continuous length of chassis assemblies 202 are cut into discrete chassis 102. The discrete chassis 102 are then rotated and advanced in the machine direction MD such that the lateral axis is parallel with the machine direction MD. The discrete chassis 102 are combined with continuous lengths of advancing first and second elastic belt substrates 206, 208. The discrete chassis 102 are then folded along the lateral axis to bring the first and second elastic belt substrates 206, 208 into a facing relationship. The first and second elastic belt substrates 206, 208 are then bonded together to form bonded regions. The first and second elastic belt substrates 206, 208 are then cut along the bonded regions to create discrete diaper pants 101.

Figure 4B:
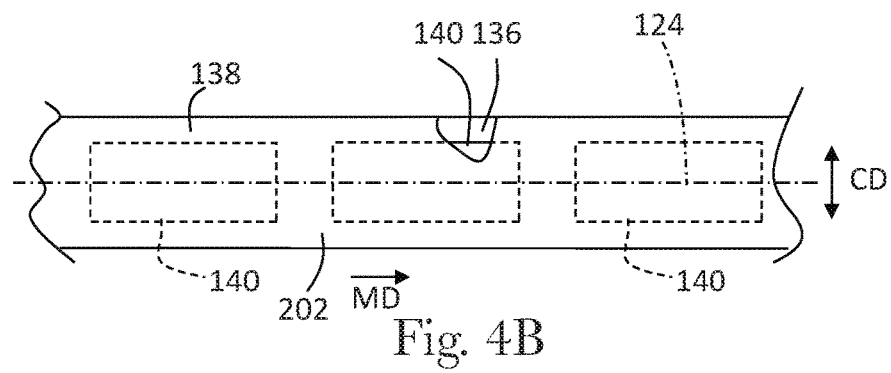
FIG. 4B is a schematic, plan view of a continuous length of chassis assemblies taken along lines 4B-4B in FIG. 4A.

As shown in FIGS. 4A and 4B, a continuous length of chassis assemblies 202 is advanced in a machine direction MD to a rotary cutting apparatus 210. The rotary cutting apparatus 210 includes a cutting roll 212 that defines a first longitudinal axis 218 and an anvil roll 214 that defines a second longitudinal axis 220. The anvil roll 214 is positioned relative to the cutting roll 212 such that the first longitudinal axis 218 is substantially parallel with the second longitudinal axis 220. The cutting roll 212 and the anvil roll 214 are defined by outer circumferential surfaces 224 and 226. A cutting member 216 may extend radially outward from the outer circumferential surface 224 of the cutting roll 212. The cutting roll 212 may be configured with vacuum pressure to hold the continuous length of chassis assemblies 202 on the cutting roll 212.

Figure 4C:
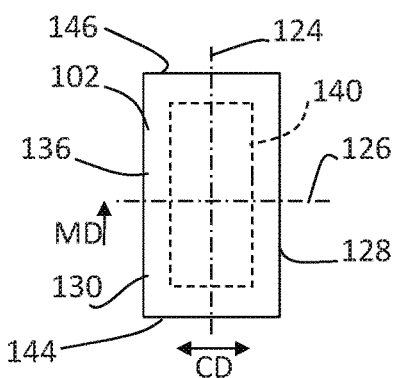
FIG. 4C is a schematic, plan view of a discrete chassis having a longitudinal axis parallel with a machine direction taken along line 4C-4C in FIG. 4A.
Figure 5:
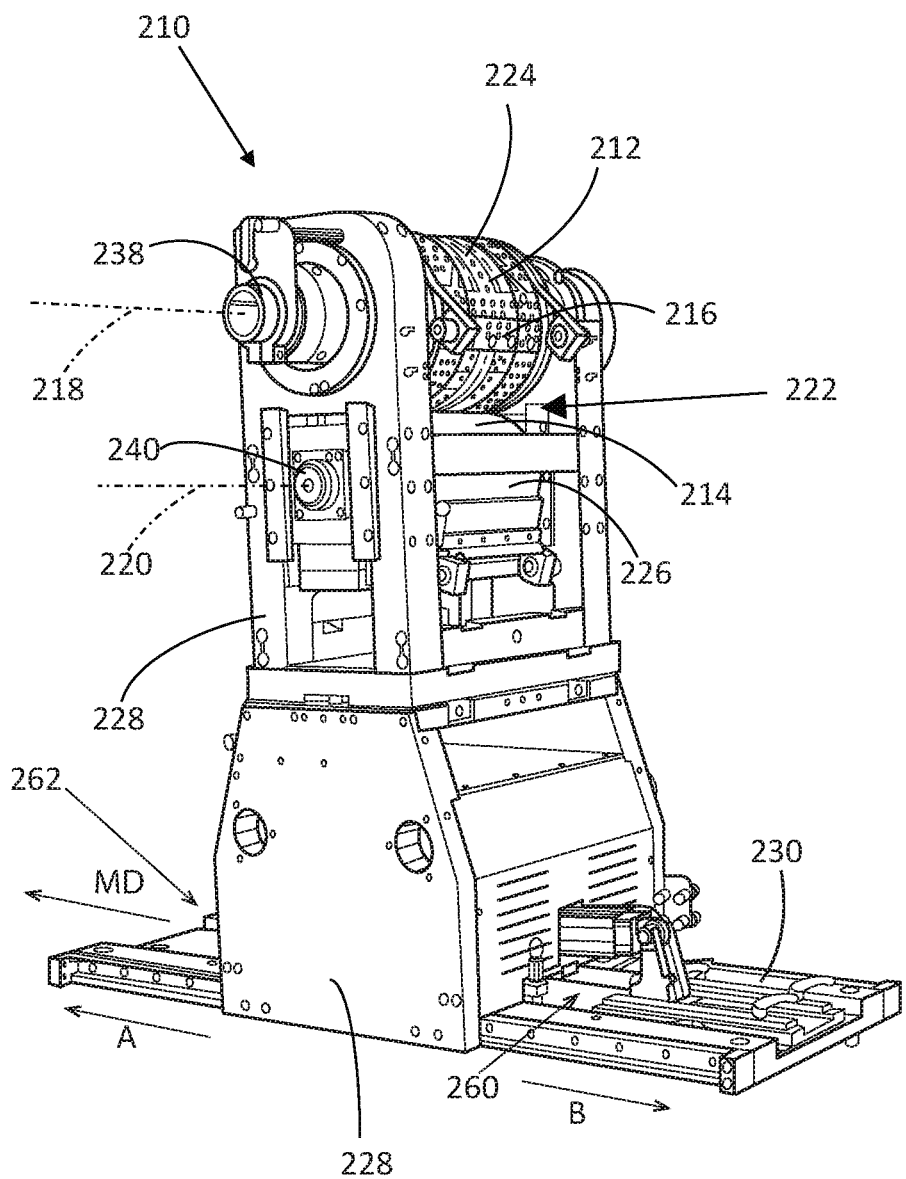
FIG. 5 is a perspective, side view of a rotary cutting apparatus.

With reference to FIGS. 4A and 5, in operation, a continuous length of chassis assemblies 202 advances onto the outer circumferential surface 224 of the cutting roll 212. The continuous length of chassis assemblies 202 advances through a nip 222 formed between the cutting roll 212 and the anvil roll 214. The cutting member 216 compresses the continuous length of chassis assemblies 202 against the outer circumferential surface 226 of the anvil roll 214. As a result, the compressive force cuts the continuous length of chassis assemblies 202 into discrete chassis 102, such as shown in FIG. 4C. In order for the cutting member 216 to rotate beyond the anvil roll 214, the cutting member 216 may be configured to flex away from the outer circumferential surface 226 of the anvil roll 214. The continuous length of chassis assemblies 202 may include absorbent assemblies sandwiched between topsheet material and backsheet material, leg elastics, barrier leg cuffs and the like.

Figure 6:
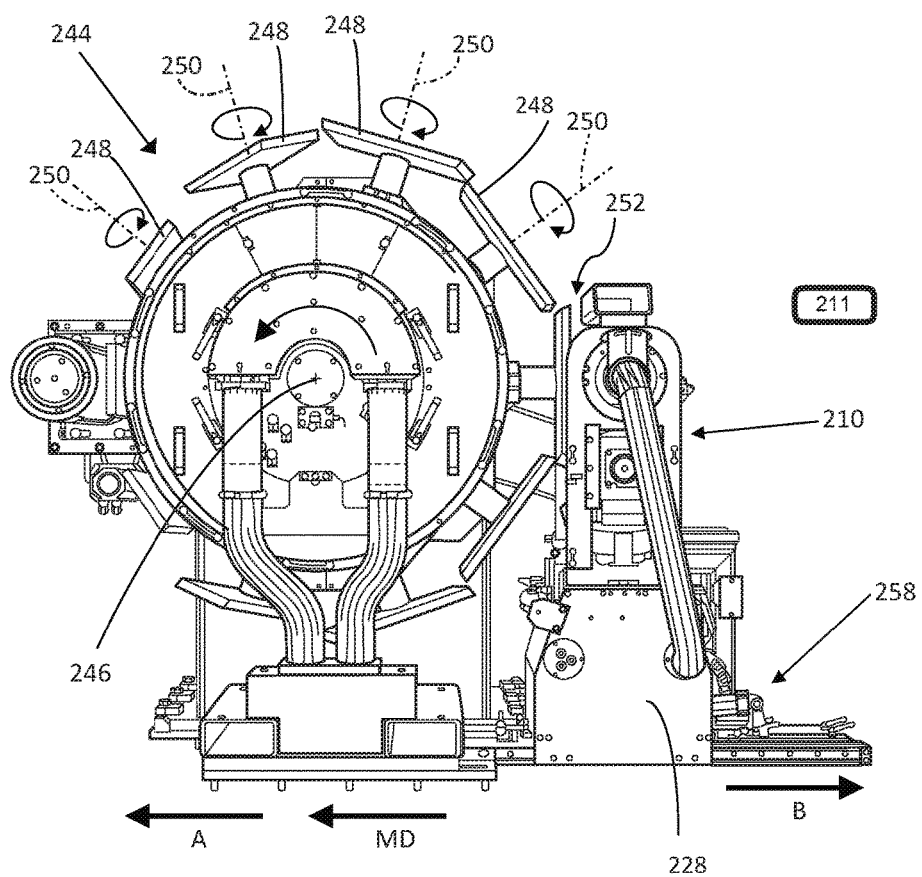
FIG. 6 is a side elevation view of a rotary cutting apparatus located adjacent to a transfer apparatus.

With continued reference to FIG. 4A, the cutting roll 212 continues to rotate and advance the discrete chassis 102 in the machine direction MD toward a gap 252 between the cutting roll 212 and the transfer apparatus 244. The discrete chassis 102 is then transferred from the cutting roll 212 to the transfer apparatus 244. With reference to FIGS. 4A and 6, the transfer apparatus 244 may rotate about a longitudinal axis 246 and may include a plurality of transfer members 248. The transfer members 248 may rotate about an axis of rotation 250 that is orthogonal to the longitudinal axis 246. As the discrete chassis 102 approaches the transfer apparatus 244, vacuum may be intermittently interrupted from the cutting roll 212. At the same time positive blow-off pressure may be applied to the discrete chassis 102 from the outer circumferential surface 224 of the cutting roll 212 to assist the discrete chassis 102 in transferring from the cutting roll 212. The transfer members 248 may be configured with vacuum to hold the discrete chassis 102. Once the discrete chassis 102 is removed from the cutting roll 212, the cutting roll 212 continues to rotate in order to advance and cut a subsequent discrete chassis.

Figure 4D:
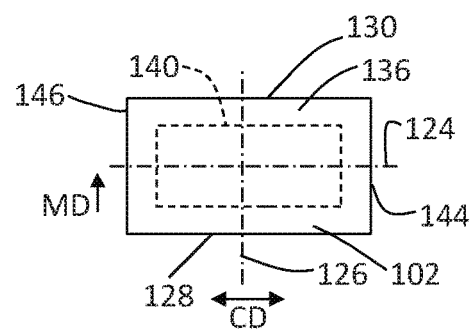
FIG. 4D is a schematic, plan view of a discrete chassis having a lateral axis parallel with the machine direction taken along line 4D-4D in FIG. 4A.

The discrete chassis 102 advances onto the transfer members 248 in the orientation shown in FIG. 4C where the longitudinal axis 124 is parallel with the machine direction MD. The transfer apparatus 244 shown in FIGS. 4A and 6 operates to advance the discrete chassis 102 in the machine direction MD while concurrently rotating the discrete chassis 102. The transfer apparatus 244 may reorient the discrete chassis 102 to the orientation shown in FIG. 4D where the lateral axis 126 is parallel with the machine direction MD. It is to be appreciated that various forms of transfer apparatuses may be used with the methods and apparatuses disclosed herein, such as methods and apparatuses for transferring discrete articles disclosed in U.S. patent application Ser. No. 13/447,531, filed on Apr. 16, 2012; U.S. patent application Ser. No. 13/447,544, filed on Apr. 16, 2012; U.S. patent application Ser. No. 13/447,568, filed on Apr. 16, 2012; and U.S. patent application Ser. No. 13/447,585, filed on Apr. 16, 2012.

Figure 4E:
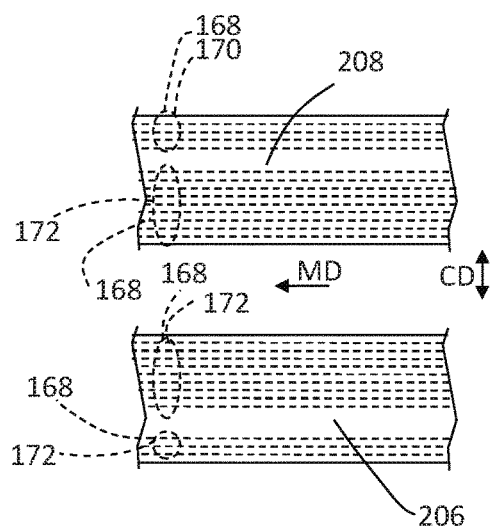
FIG. 4E is a schematic, plan view of continuous lengths of first and second elastic belt substrates taken along lines 4E-4E in FIG. 4A.
Figure 4F:
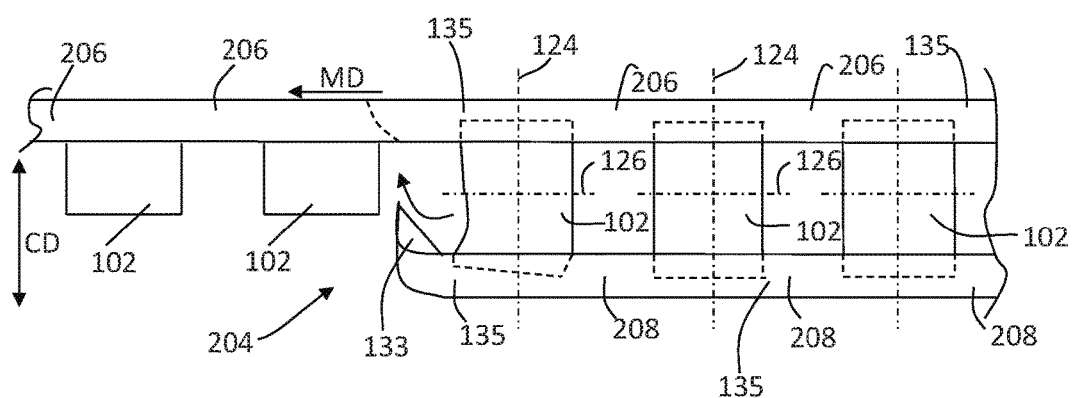
FIG. 4F is a schematic, plan view of a continuous length of diaper pants taken along line 4F-4F in FIG. 4A.

As shown in FIG. 4A, the discrete chassis 102 is transferred from the transfer apparatus 244 and combined with advancing, continuous lengths of first and second belt substrates 206, 208, such as shown in FIG. 4E. The continuous lengths of first and second belt substrates 206, 208 are subsequently cut to form first and second elastic belts 106, 108. The discrete chassis 102 is transferred from the transfer apparatus 244 to a nip 234 formed between the transfer apparatus 244 and a carrier apparatus 236. At the nip 234, the discrete chassis 102 is combined with the continuous lengths of advancing first and second belt substrates 206, 208 to form a continuous length of absorbent articles 204. As shown in FIG. 4F, a wearer facing surface 133 of the first belt substrate 206 may be joined with the garment facing surface 134 of the chassis 102 along the first waist region 116, and a wearer facing surface 133 of the second belt substrate 208 may be joined with the garment facing surface 134 of the chassis 102 along the second waist region 118. As shown in FIG. 4A, adhesive 190 may be applied to the wearer facing surface 133 of the first and second belt substrates 206, 208 using an adhesive applicator 192 before combining with the discrete chassis 102 at the nip 234. With reference to FIG. 4F, a continuous length of absorbent articles 204 is defined by multiple discrete chassis 102 spaced apart from each other along the machine direction MD and connected with each other by the first and second belt substrates 206, 208.

As shown in FIG. 4A, the continuous length of absorbent articles 204 advances from the nip 234 to a folding apparatus 254. With reference to FIGS. 2A, 3A, and 4F, at the folding apparatus 254, each chassis 102 is folded in the cross direction CD along a lateral axis 126 to place the first waist region 116, and specifically, the inner, wearer facing surface 132 into a facing, surface to surface arrangement with the inner, wear facing surface 132 of the second waist region 118. With reference to FIGS. 2A and 4F, the folding of the chassis 102 also positions the wearer facing surface 133 of the first belt substrate 206 in a facing relationship with the wearer facing surface 133 of the second belt substrate 208.

Figure 4G:
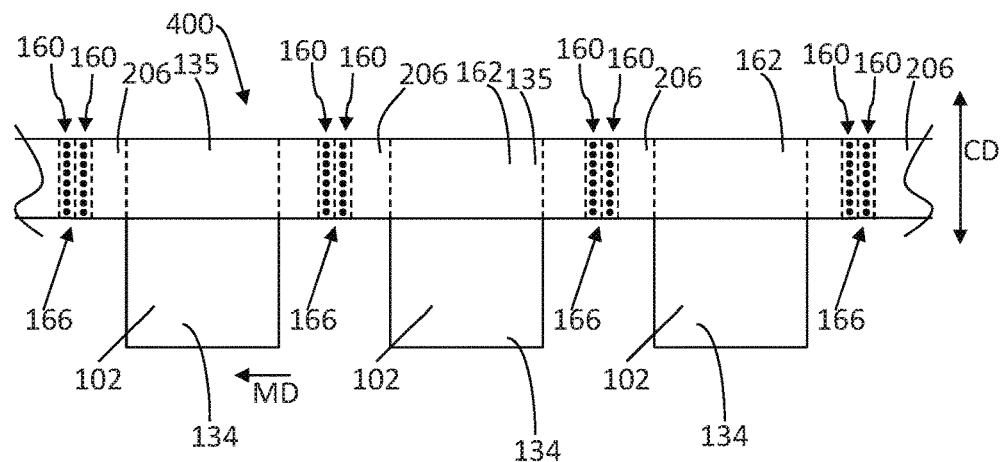
FIG. 4G is a schematic, plan view of a continuous length of folded diaper pants taken along line 4G-4G in FIG. 4A.
Figure 4H:
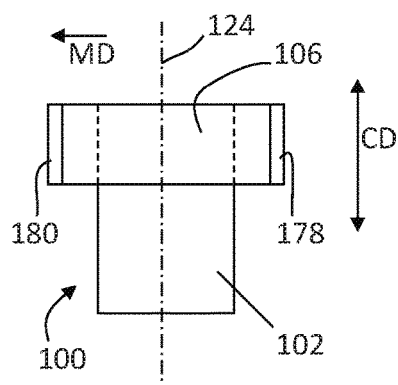
FIG. 4H is a schematic, plan view of a discrete diaper pant taken along line 4H-4H in FIG. 4A.

Referring to FIG. 4A, the folded discrete chassis 102 connected with the first and second belt substrates 206, 208 is advanced from the folding apparatus 254 to a bonder apparatus 256. The bonder apparatus 256 operates to bond an overlap area 166 of the first and second belt substrates 206, 208, thus creating discrete bonded regions 160, as shown in FIG. 4G. The overlap area 166 includes a portion of the first belt substrate 206 extending between each chassis 102 and a portion of the second belt substrate 208 extending between each chassis 102. As shown in FIG. 4A, the continuous length of absorbent articles 204 are advanced from the bonder apparatus 256 to a cutter 286, shown in the form of a cutting roll for purposes of illustration, where the bonded regions 160 are cut into along the cross direction CD to create a first side seam 178 on a diaper pant 101 and a second side seam 180 on a subsequently advancing diaper pant 101, such as shown in FIG. 4H.

As shown in FIG. 5, the cutting roll 212 and the anvil roll 214 may be configured to rotate about a first longitudinal axis 218 and a second longitudinal axis 220. Referring to FIG. 5, in some exemplary configurations, the cutting roll 212 may be connected with a shaft 238 and the anvil roll 214 may be connected with a shaft 240. The cutting roll 212 and the anvil roll 214 may be connected with shafts 238, 240 using fixed-floating bearings, for example, that allow for the expansion of components during extended operation. In some exemplary configurations, the anvil roll 214 may rotate independent from the cutting roll 212. For example, the cutting roll 212 and/or the anvil roll 214 may be configured to rotate using gears, belts, or direct couplings. In other exemplary configurations, the anvil roll 214 may be driven by bearer rings on the cutting roll 212. As such, the anvil roll 214 may be a "walking" type anvil roll.

Figure 7:
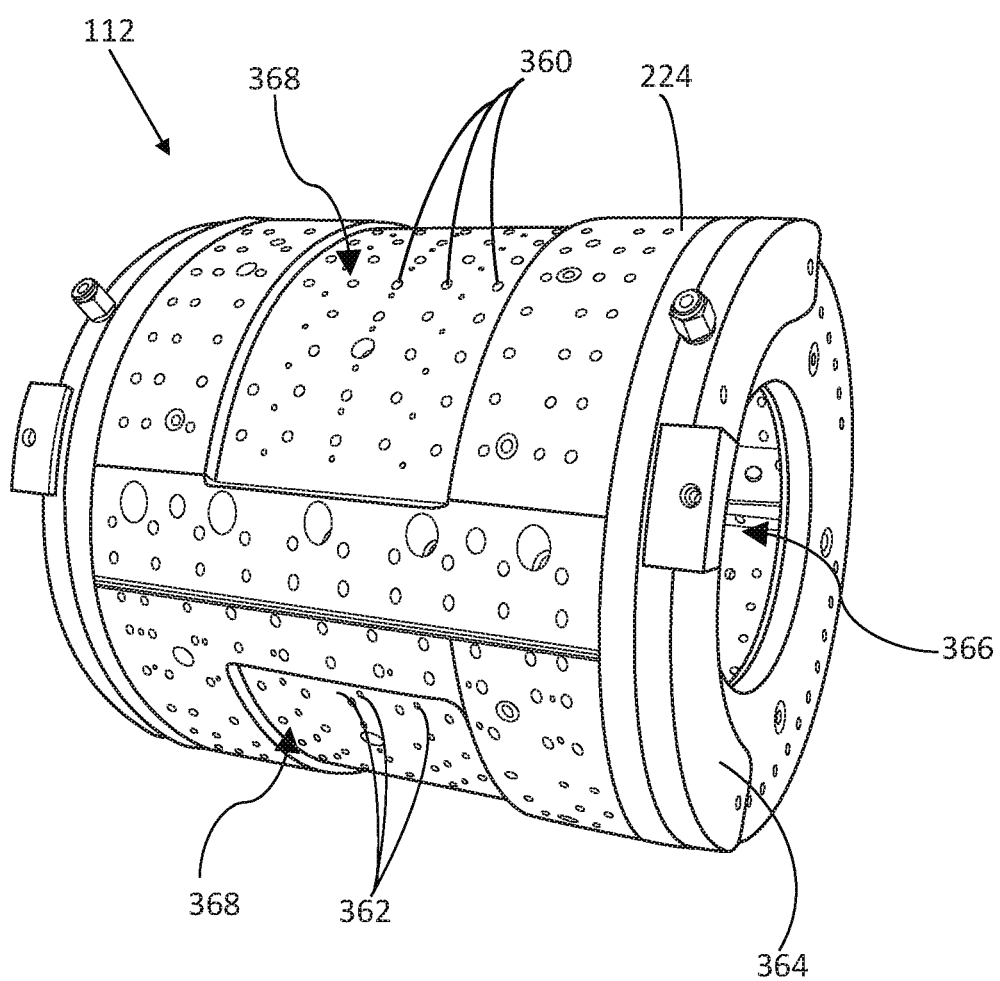
FIG. 7 is a perspective view of a cutting roll.

As previously mentioned, the cutting roll 212 may be configured to apply vacuum pressure to the chassis assemblies advancing on the outer circumferential surface 224 of the cutting roll 212. For example, as shown in FIG. 7, the cutting roll 212 may include a plurality of vacuum apertures 360 in the outer circumferential surface 224. Vacuum may be supplied to the vacuum apertures 360 from a vacuum source. For example, negative, vacuum pressure may enter the cutting roll 212 through the center 366 of the cutting roll 212. It is to be appreciated that negative, vacuum pressure may enter the cutting roll 212 at various locations on the cutting roll 212.

With reference to FIGS. 5-7, in some exemplary configurations, vacuum may be intermittently interrupted from the cutting roll 212 in order to assist the discrete chassis assemblies in transferring from the cutting roll 212 to the transfer apparatus 244. Once vacuum pressure is turned off to the cutting roll 212, the negative, vacuum pressure may be canceled by introducing compressed air to the vacuum apertures 360. For example, compressed air may enter through the center 366 of the cutting roll 212 at the same location where the vacuum pressure enters the cutting roll 212. The compressed air acts to increase the pressure applied through the vacuum apertures 360 to atmospheric or near atmospheric air pressure.

The cutting roll 212 may also be configured to apply positive, blow-off pressure to the discrete chassis assemblies in order to assist the discrete chassis assemblies in transferring from the cutting roll 212 to the transfer apparatus 244. As shown in FIG. 7, the cutting roll 212 may include a plurality of blow-off apertures 362 in the outer circumferential surface 224. In some exemplary configurations, positive, blow-off pressure may be applied to the chassis assemblies through the blow-off apertures 362. Compressed air may enter the cutting roll 212 through a blow-off manifold 364 that is connected with the cutting roll 212. The compressed or atmospheric air may apply a positive force to the discrete chassis assemblies through the blow-off apertures 362. As a result, the discrete chassis assemblies may move away from the outer circumferential surface 224 of the cutting roll 212. Referring to FIGS. 4A and 7, the blow-off manifold 364 may be configured to apply a positive force to the chassis assembly for a portion of the time that the discrete chassis advances on the cutting roll 212. For example, the blow-off manifold 364 may be configured to apply positive force to the discrete chassis 102 assembly as the discrete chassis 102 is advancing through the gap 252 between the cutting roll 212 to the transfer apparatus 244.

It is to be appreciated that the vacuum pressure and blow-off pressure may be controlled independently of each other in order to control the movement of the discrete chassis 102 as the discrete chassis 102 advances on the outer circumferential surface 224 of the cutting roll 212.

Figure 8:
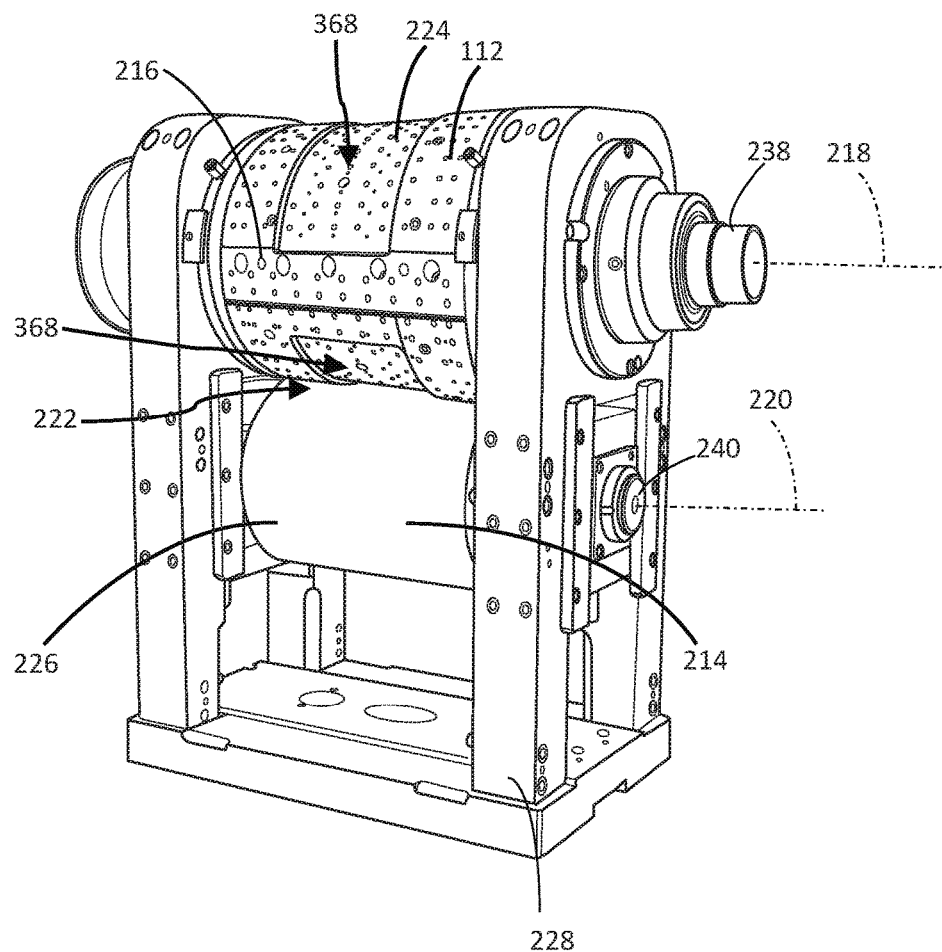
FIG. 8 is a perspective view of a portion of a rotary cutting apparatus.

The outer circumferential surface 224 of the cutting roll 212 may include one or more recessed regions 368 as shown in FIG. 7. The recessed regions 368 may be configured to hold an absorbent assembly of a discrete chassis. The recessed regions 368 may allow the absorbent assembly to expand in caliper as the chassis assemblies advance on the cutting roll 212. Referring to FIG. 8, the recessed regions 368 may reduce the compressive force applied to the absorbent assemblies as the chassis assemblies advance through the nip 222 between the cutting roll 212 and the anvil roll 214.

In some exemplary configurations, the outer circumferential surface 224 of the cutting roll 212 may be configured to have a relatively high coefficient of friction to assist the cutting roll 212 in holding the discrete chassis in a fully extended configuration. For example, the outer circumferential surface 224 of the cutting roll 212 may be plasma coated.

Referring to FIG. 8, the cutting member 216 may comprise various materials that are capable of flexing away from the outer circumferential surface 226 of the anvil roll 214. For example, the cutting member 216 may comprise tungsten carbide or tool steel. In other exemplary configurations, the cutting member 216 may comprise a rigid material. In an exemplary configuration where the cutting member 216 comprises a rigid material, the rotary cutting apparatus may be configured as a rotary die cutter. In an exemplary configuration where the cutting member is made of a rigid material, the cutting roll 212 may be configured with a spring, such as a goose-neck spring. The spring may flex when the cutting member 216 compresses the continuous length of chassis assemblies 202 against the outer circumferential surface 226 of the anvil roll 214 in order to advance the cutting member 216 past the outer circumferential surface 226 of the anvil roll 214.

The anvil roll 214 may comprise various materials, such as tungsten carbide or tool steel. The outer circumferential surface 226 of the anvil roll 214 may comprise various materials that are integral with, or separate from, the anvil roll 214 material.

As shown in FIG. 8, in some exemplary configurations, the cutting roll 212 may be fixed to a frame 228 and the anvil roll 214 may be loaded to the cutting roll 212. In other exemplary configurations, the anvil roll 214 may be fixed to the frame 228 and the cutting roll 212 may be loaded to the anvil roll 214. Various systems may be used to load the anvil roll 214 to the cutting roll 212 or to load the cutting roll 212 to the anvil roll 214. For example, loading systems may include pneumatic cylinders, hydraulic systems, air-over-oil systems, springs, linkages, or actuators. It is to be appreciated that the distance from the axis of rotation 218 of the cutting roll 212 and the axis of rotation 220 of the anvil roll 214 may affect the force applied to the continuous length of chassis assemblies by the cutting member 216.

Referring to FIGS. 4A and 6-8, during operation, the continuous length of chassis assemblies 202 advances onto the outer circumferential surface 224 of the cutting roll 212. Vacuum may be applied to the chassis assemblies 202 through the vacuum apertures 360 in the cutting roll 212. As the continuous length of chassis assemblies 202 advance through the nip 222 between the cutting roll 212 and the anvil roll 214, the cutting member 216 compresses the chassis assemblies 202 against the outer circumferential surface 226 of the anvil roll 214. The force of the cutting member 216 compressing the chassis assemblies 202 against the anvil roll 214 cuts the continuous length of chassis assemblies 202 into discrete chassis 102. Vacuum may be used to hold the discrete chassis in an extended configuration.

Next, the discrete chassis 102 is transferred to the transfer apparatus 244. The discrete chassis 102 advances through the gap 252 between the cutting roll 212 and the transfer apparatus 244. Positive air pressure may be introduced through the center 366 of the cutting roll 212 in order to cancel the vacuum pressure applied through the vacuum apertures 360. In addition, positive air pressure may be applied through the blow-off manifold 364, to the blow-off apertures 362, and then to the discrete chassis 102. As positive air pressure is applied to the discrete chassis 102, vacuum pressure may be applied to the discrete chassis 102 by the transfer members 248 of the transfer apparatus 244. As a result, the discrete chassis 102 transfers from the cutting roll 212 to the transfer member 248.

As discussed above, various defective operating conditions may cause continuous length of chassis assemblies 202 to be incompletely cut by the cutting apparatus 210. For example, the cutting member 216 may become dull through extended use. In another example, the outer circumferential surface 224 of cutting roll 212 and/or the cutting member 216 may become contaminated with materials, such as adhesive. As a result, the continuous length of chassis assemblies 202 may not transfer to the transfer apparatus 244, but, instead, the continuous length of chassis assemblies 202 may begin to undesirably wrap around the cutting roll 212. The continuous length of chassis assemblies 202 may continue to wrap around the cutting roll 212 such that the continuous length of chassis web 202 expands radially around the outer circumferential surface 224 of the cutting roll 212 and begins to fill the gap 252 between the cutting roll 212 and the transfer apparatus 244. As such, the transfer apparatus 244 may collide with the wrapped chassis assemblies 202, which in turn, may induce a relatively high force on the rotary cutting apparatus 210 and the transfer apparatus 244 at the gap 252. Consequently, the cutting roll 212 and/or adjacent equipment may be damaged. As mentioned above, and as discussed in more detail below, the rotary cutting apparatus 210 may be configured with modes of operation that allows the gap 252 to increase in length such that the continuous length of chassis web 202 may continue wrapping around the cutting roll 212 without interfering with the transfer apparatus 244 until the converting apparatus 200 can be safely shut down.

For example, the rotary cutting apparatus 210 shown in FIGS. 5 and 6 may be configured in two modes of operation. In particular, the rotary cutting apparatus 210 may be configured in a first mode of operation, referred to as an operating configuration, where the rotary cutting apparatus 210 is configured to cut the continuous length of chassis assemblies into discrete chassis. In a second mode of operation, referred to as a fail-safe configuration, the rotary cutting apparatus 210 is configured to adjust the length of the gap 252 to prevent damage to the rotary cutting apparatus 210 and/or adjacent equipment. As shown in FIG. 5, the rotary cutting apparatus 210 may include a frame 228 that is movable in a first direction, A, and in a second direction B, wherein the first direction A is opposite the second direction, B. The first direction, A, may be the machine direction MD. The frame 228 may be moveably connected with a track 230. The rotary cutting apparatus 210 may include a cutting roll 212 defining a first longitudinal axis 218. The cutting roll 212 may be rotatably connected with the frame 228 and configured to rotate about the first longitudinal axis 218. The rotary cutting apparatus 210 may include an anvil roll 214 defining a second longitudinal axis 220. The anvil roll 214 may be rotatably connected with the frame 228 and configured to rotate about the second longitudinal axis 220. The anvil roll 214 may be positioned relative to the cutting roll 212 such that the first longitudinal axis 218 is substantially parallel with the second longitudinal axis 220. The first longitudinal axis 218 and the second longitudinal axis 220 may be orthogonal to the first and second directions, A and B. A nip 222 is formed between the anvil roll 214 and the cutting roll 212.

Figure 9:
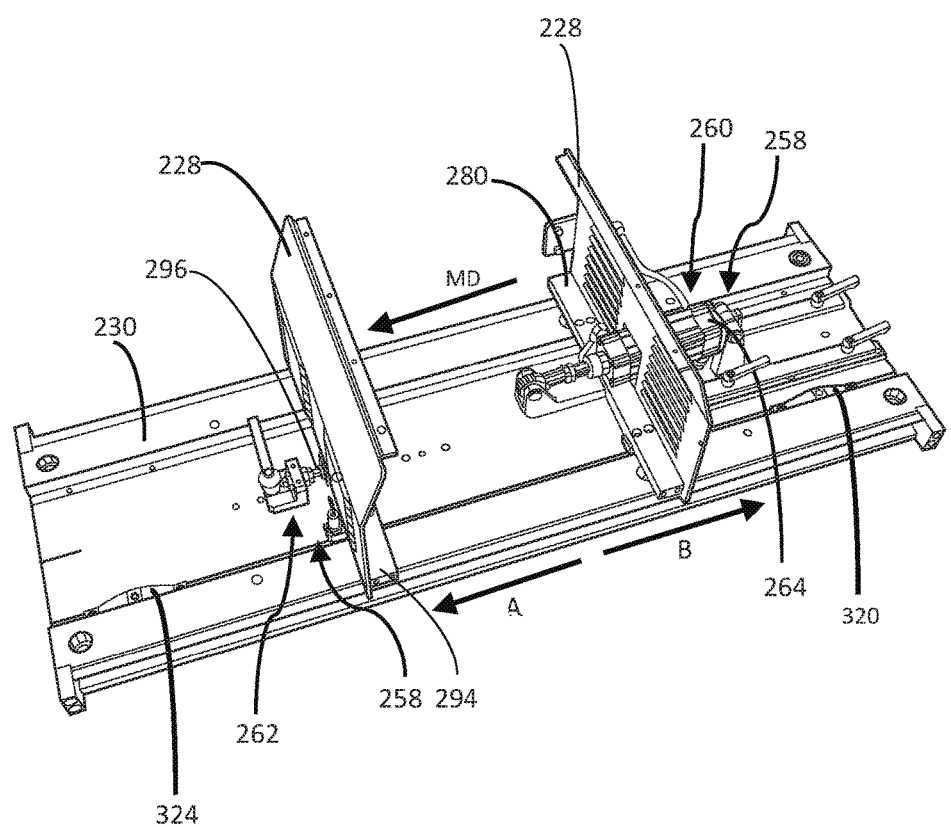
FIG. 9 is a perspective view of a first blocking member and a second blocking member connected with a track of a rotary cutting apparatus.

As shown in FIG. 9, the rotary cutting apparatus 210 may include a first blocking member 262 and a second blocking member 260. The first blocking member 262 may be connected with one end of the track 230 and the second blocking member 260 may be connected with the opposite end of the track 230. The first blocking member 262 may be adapted to limit the movement of the frame 228 in the first direction, A. The second blocking member 260 may be adapted to limit movement of the frame 228 in the second direction, B. In addition, the second blocking member 260 may be adapted to apply a positive force to the frame 228 in the first direction, A, to hold the frame 228 against the first blocking member 262. As such, with the rotary cutting apparatus in an operating configuration, the first blocking member 262 and the second blocking member 260 operate to fix the frame 228 in a desired location.

Figure 10:
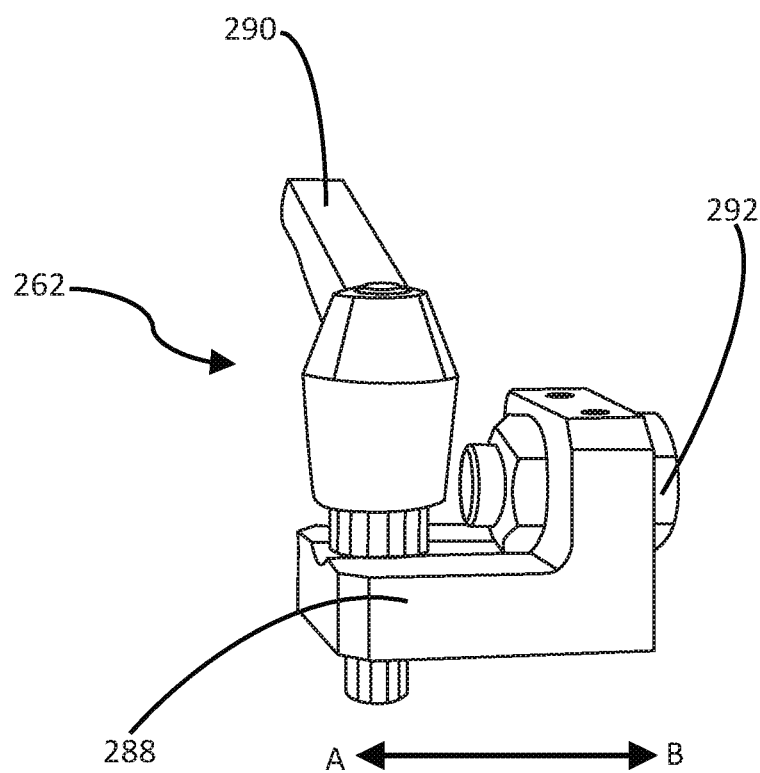
FIG. 10 is a perspective view of a first blocking member.
Figure 11:
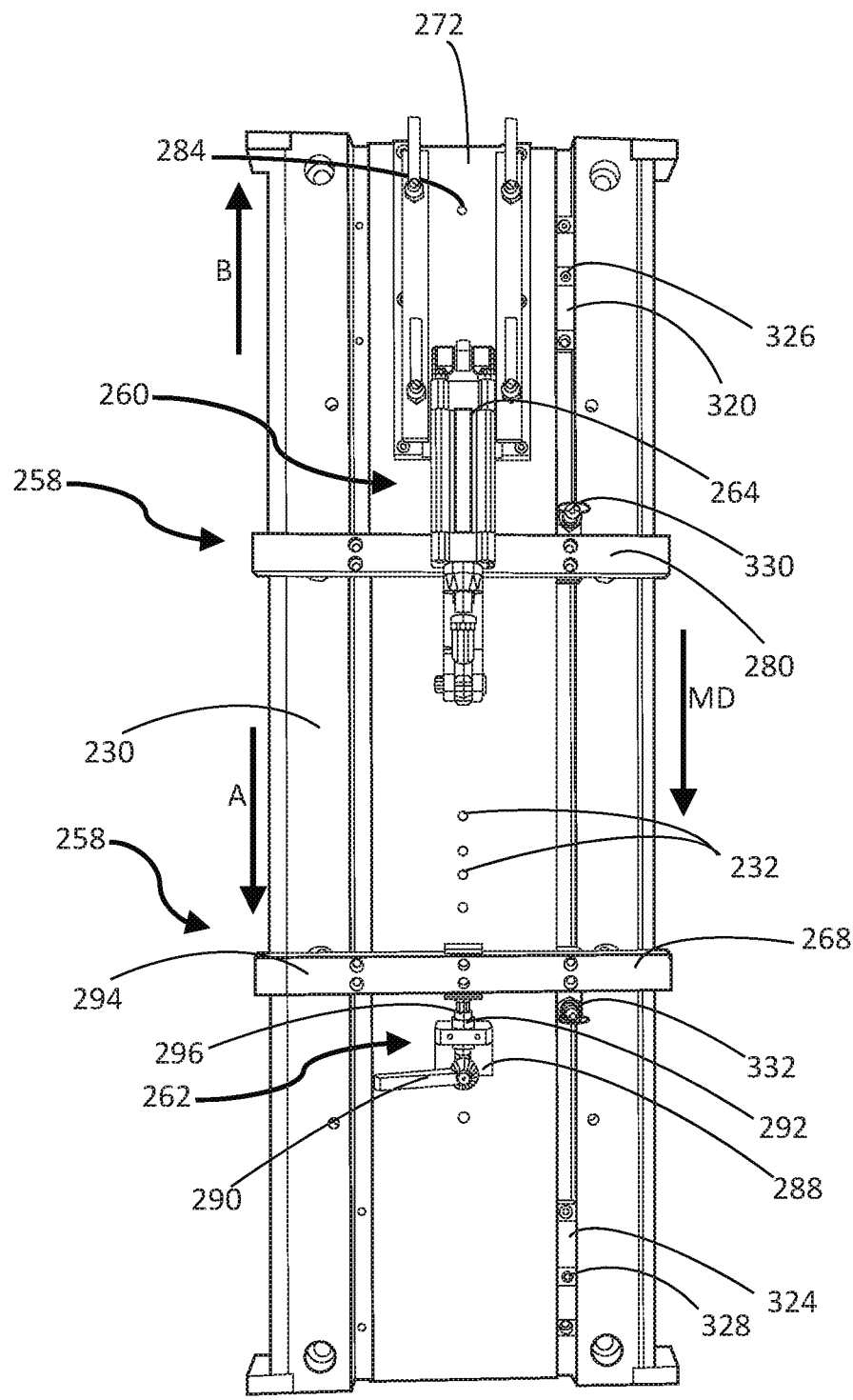
FIG. 11 is a plan view of a first blocking member and a second blocking member connected with a track of a rotary cutting apparatus.

With reference to FIGS. 9-11, a first blocking member 262 that is selectively connectable with locking apertures 232 on the track 230. For clarity, various components, such as the frame, are not shown in FIGS. 9-11. The first blocking member 262 includes a locking member 290 connected with a base 288. The locking member 290 may be adapted to selectively connect with each locking apertures 232 on the track 230. The first blocking member 262 also includes a stop member 292 that extends in the second direction, B. As discussed in more detail below, the stop member 292 may align with a stop member 296 that is connected with the frame 228. The stop member 296 may be connected with a joining member 294 that is connected with the frame 228.

Figure 12:
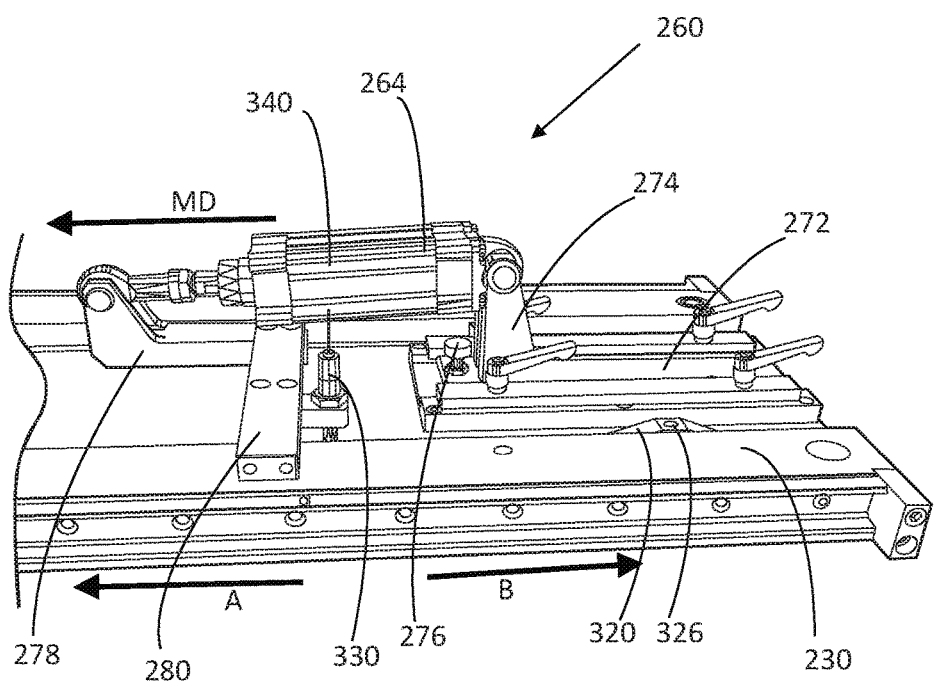
FIG. 12 is a perspective view of a second blocking member connected with a track of a rotary cutting apparatus.

As previously mentioned, the rotary cutting apparatus 210 may include a second blocking member 260, such as shown in FIGS. 5, 11, and 12. The second blocking member 260 may be configured in a first configuration and in a second configuration. When the rotary cutting apparatus 210 is configured in an operating configuration, the second blocking member 260 may be configured in the first configuration. As shown in FIGS. 5 and 11, in the first configuration, the second blocking member 260 is adapted to limit the movement of the frame 228 in the second direction, B. The second blocking member 260 may be configured to also apply a positive force to the frame 228 in the first direction, A. When the rotary cutting apparatus 210 is configured in a fail-safe configuration, the second blocking member 260 may be configured in a second configuration. In a second configuration, the second blocking member 260 is adapted to allow the frame 228 to move in the second direction, B, on the track 230.

With continuing reference to FIGS. 5, 11, and 12, the second blocking member may include a base 272 that is connected with the track 230 of the rotary cutting apparatus 210. The second blocking member 260 may also include a first arm 274. The first arm 274 may be connected with the base 272 at one end and with a reciprocating member 264 at an opposite end of the first arm 274. The first arm 274 may be moveably connected with the base 272. For example, the first arm 274 may be slideably connected with the base 272. A locking member 276 may be used to fix the first arm 274 with the base 272. The reciprocating member 264 may be pivotally connected with the first arm 274 at one end and pivotally connected with a second arm 278 at an opposite end of the reciprocating member 264. The second arm 278 may be connected with a joining member 280. The joining member 280 may be connected with the frame 228 of the rotary cutting apparatus 210, such as shown in FIG. 9.

Figure 13:
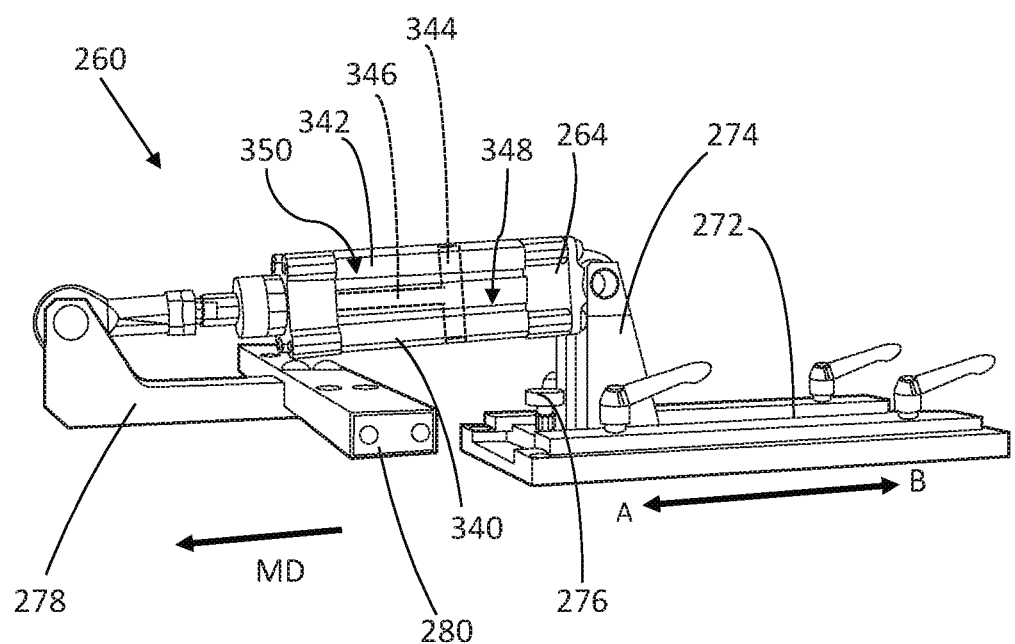
FIG. 13 is a perspective view of a second blocking member.
Figure 14:
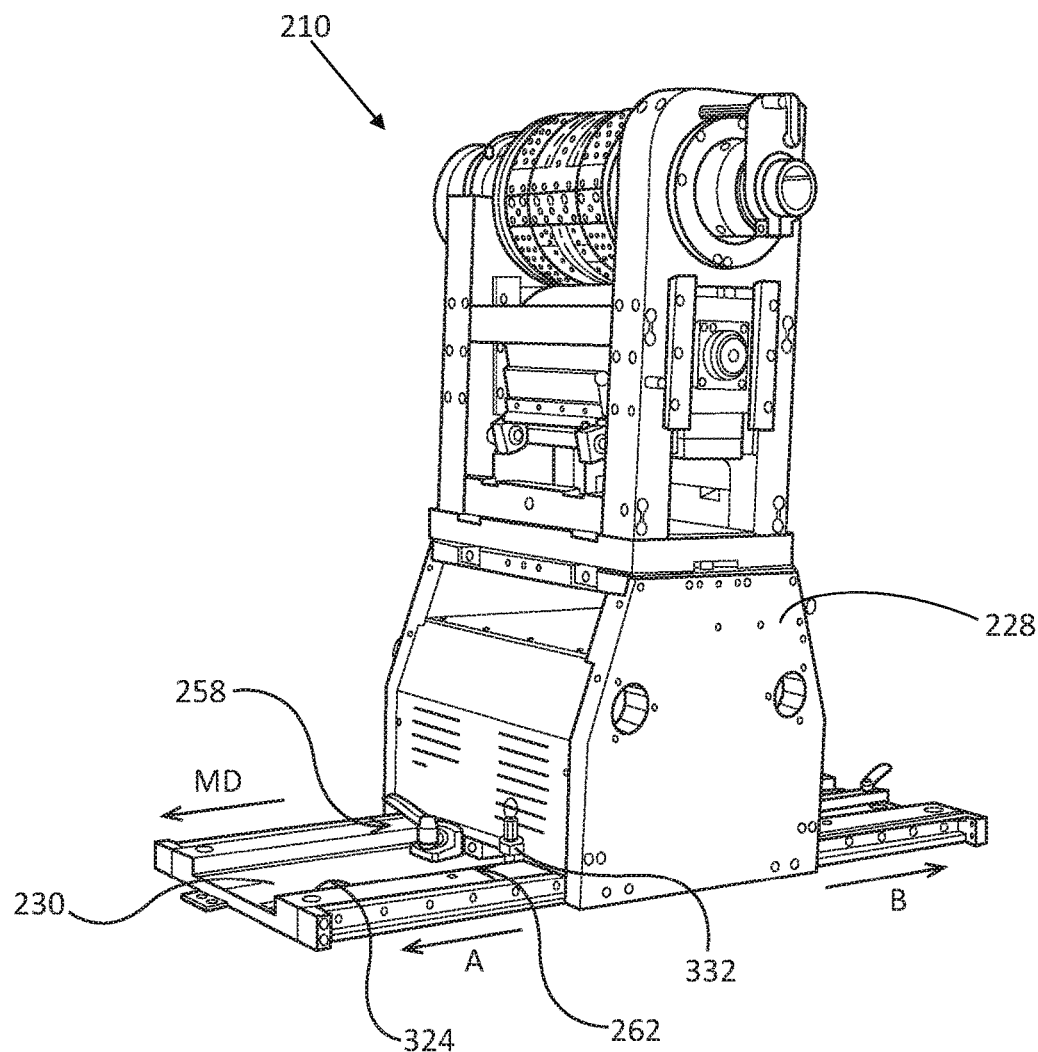
FIG. 14 is a perspective view of a rotary cutting apparatus.

The reciprocating member may be configured in various ways. For example, as shown in FIGS. 12 and 13, the reciprocating member 264 may be configured as a pneumatic cylinder 340. The pneumatic cylinder 340 includes a cylinder barrel 342, a piston 344, and a piston rod 346 connected with the piston 344 as shown in FIG. 13. The piston 344 may be located inside of the cylinder barrel 342 and may separate the inside of the cylinder barrel 342 into a first chamber 348 and a second chamber 350. The piston rod 346 may be connected to the piston 344 and may extend in the first direction A, through the second chamber 350. Exemplary pneumatic cylinders are manufactured by Festo Corporation of Hauppauge, N.Y., model 163368, DNC-50-75-PPV-A. While FIGS. 12 and 13 show the reciprocating member in the form of a pneumatic cylinder, it is to be appreciated that the reciprocating member may comprise various other apparatuses, such as a spring(s), hydraulic cylinder, four bar linkage mechanism, air-over-oil systems, and the like. The reciprocating member may be made of a variety of rigid materials, such as steel.

Referring to FIGS. 5, 6, 9, and 11, the rotary cutting apparatus 210 may be configured with a sensor 211. The sensor is adapted to detect a defective operating configuration, such as the continuous length of chassis assemblies wrapping around the cutting roll 212. As discussed in more detail below, the sensor is configured to send a signal to the second blocking member 260 if a defective operating condition is detected. In response, the reciprocating member 264 of the second blocking member 260 stops applying force to the frame 228 in the first direction, A. As such, the pressure applied to the cutting roll 212 and the transfer apparatus 244 will cause the frame 228 of the rotary cutting apparatus 210 to slide on the track 230, away from the transfer apparatus 244. The sensor may be configured as a camera or a photo-eye that detects changes in contrast to the continuous length of chassis assemblies. In some exemplary configurations, the sensor may be configured as an accelerometer that detects levels of vibration. In other exemplary configurations, the sensor may be configured as a pressure sensor that detects changes in pressure at the gap between the cutting roll and the transfer apparatus. In some exemplary configurations, the sensor may be configured to detect motor current overload.

With the rotary cutting apparatus 210 in an operating configuration, as shown in FIG. 9, the second blocking member 260 is configured to apply a positive force to the frame 228 in the first direction, A. Referring to FIGS. 9-13, in order to apply a positive force to the frame 228 in the first direction A, compressed air is directed into the first chamber 348 of the cylinder barrel 342. The compressed air expands in the first chamber 348 and forces the piston 344, and thus the piston rod 346, in the first direction, A. As the piston rod 346 moves in the first direction, A, the second arm 278, the joining member 280, and the frame 228 concurrently move in the first direction, A. The stop member 292 of the first blocking member 262 is configured to contact the stop member 296 connected with the frame 228. The location of the first blocking member 262 on the track 230 determines how far the frame 228 can move in the first direction, A. As a result, the frame 228 is held in an operating configuration for as long as the reciprocating member 264 applies a positive force to the frame 228 in the first direction, A.

With reference to FIGS. 4A, 5, 11-13, in the event that the sensor detects that the continuous length of chassis assemblies 202 is wrapping around the cutting roll 212, a signal is sent to the second blocking member 260. Once a signal is received by the second blocking member 260, the second blocking member 260 is configured to stop directing compressed air to the first chamber 348 of the cylinder barrel 342 of the reciprocating member 264. As such, the frame 228 of the rotary cutting apparatus 210 is free to move in the second direction, B, away from the first blocking member 262. If the continuous length of chassis assemblies wrap around the cutting roll 212 to an extent that the chassis assemblies 202 fill the gap 252 between the cutting roll 212 and the transfer apparatus 244, the chassis assemblies 202 may apply a force to the cutting roll 212, thereby causing the frame 228 to move upstream on the track 230. As the frame 228 moves upstream, the piston rod 346, and thus the piston 344, move upstream. In some exemplary configurations, compressed air may be directed into the second chamber 350 of the cylinder barrel 342 in order to move the piston 344 and piston rod 346, upstream. As discussed in more detail below, the rotary cutting apparatus 210 may comprise a fourth blocking member 320 that limits movement of the frame 228 in the second direction, B, in order to prevent the frame 228 from sliding off of the track 230.

Referring to FIGS. 5 and 11, the frame 228 may be selectively positionable at various locations on the track 230. For example, the frame 228 may be moved to perform maintenance on the converting apparatus 200 and/or to reposition the rotary cutting apparatus 210 for manufacturing a different size diaper pant. In particular, the frame 228 of the rotary cutting apparatus 210 may be configured to move in the first and second directions, A and B. In order to limit movement of the frame 228 in the first and second directions, A and B, on the track 230, the rotary cutting apparatus 210 may include a third blocking member 324 and a fourth blocking member 320, such as shown in FIG. 11. The third blocking member 324 and the fourth blocking member 320 may include stop apertures 328 and 326, respectively. The rotary cutting apparatus 210 may include stop pins 332 and 330. The stop pin 332 may be connected with the joining member 294 that is connected with the frame of the rotary cutting apparatus 210. The stop pin 332 may align with the stop aperture 328 of the third blocking member 324. The stop pin 332 may be releasably connectable with the stop aperture 328 of the third blocking member 324. The stop pin 330 may align with the stop aperture 326 of the fourth blocking member 320. The stop pin 330 may be connected with the joining member 280 that is connected with the frame of the rotary cutting apparatus 210. The stop pin 330 may be releasably connectable with the stop aperture 326 of the fourth blocking member 320.

The third and fourth blocking members 324 and 320 prevent the frame 228 from sliding off of the track 230 as the frame 228 moves in the first and second directions A and B on the track 230. If the stop pin 332 aligns with the stop aperture 328 of the third blocking member 324, the stop pin 332 will engage the stop aperture 328 of the third blocking member 324 and prevent the frame from moving beyond the third blocking member 324 in the first direction A. Likewise, if the stop pin 330 aligns with the stop aperture 326 of the fourth blocking member 320, the stop pin 330 will engage the stop aperture 326 of the fourth blocking member 320 and prevent the frame from moving beyond the fourth blocking member 320 in the second direction, B.

In order to move the frame 228 of the rotary cutting apparatus 210 in the first or second directions, A or B, the first and second blocking members 262 and 260 may be repositioned on the track 230. With reference to FIGS. 9, 11, and 12, the first arm 274 of the second blocking member 260 may be moveably connected with the base 272. The locking member 276 of the second blocking member 260 may be releasably connectable with one or more of apertures 284 in the base 272. The locking member 276 may be disengaged from the aperture 284 in the base 272 and the first arm 274 may slide on the base 272 in the first direction, A, or the second direction, B. As the first arm 274 moves on the base 272, the reciprocating member 264, the second arm 278, the joining member 280, and the frame 228 move in the first or second direction, A or B, on the track 230.

The first blocking member 262 may also be repositioned on the track 230. The first blocking member 262 may be repositioned by disengaging the locking member 290 and removing the base 288 from the track 230. The first blocking member 262 may be repositioned by locking the base 288 into a different aperture 232 in the track 230. The frame 228 may slide on the track 230 to reposition the frame 228 relative to the first blocking member 262.

In some exemplary configurations, the transfer apparatus may be compliant. In such an exemplary configuration, the transfer apparatus may be configured to relieve the compressive force applied to the transfer apparatus by a continuous length of chassis web wrapping around the cutting roll. For example, the transfer apparatus may be configured as a conveyor; a continuous web of material supported by rollers located adjacent to the nip; or a drum. The transfer apparatus may include a compliant material such as rubber, silicone, or urethane that is configured to deform as a result of the force applied to the transfer apparatus and the cutting roll by the continuous length of chassis assemblies wrapping around the cutting roll. In other exemplary configurations, in order to relieve the force applied by the chassis assemblies, the transfer apparatus may be spring loaded. In some exemplary configurations, the cutting roll may be spring loaded against the gap between the cutting roll and the transfer apparatus in order to relieve the compression applied by the chassis assemblies.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A rotary cutting apparatus comprising:
    a frame movable in a first direction and a second direction, wherein the first direction is opposite the second direction, wherein the first direction and the second direction are horizontal;
    a cutting roll defining a first longitudinal axis, wherein the cutting roll is rotatably connected with the frame and configured to rotate about the first longitudinal axis;
    an anvil roll defining a second longitudinal axis, wherein the anvil roll is rotatably connected with the frame and configured to rotate about the second longitudinal axis, the anvil roll positioned relative to the cutting roll such that the first longitudinal axis is substantially parallel with the second longitudinal axis;
    a first blocking member adapted to prevent movement of the frame in the first direction, wherein the first blocking member is configured to engage a portion of the frame;
    a second blocking member connected with the frame, the second blocking member comprising a base, a first arm connected with the base, a reciprocating member comprising a first end portion pivotally connected to the first arm and a second end portion pivotally connected to a second arm, wherein the second blocking member comprises first and second configurations, wherein the second blocking member is adapted to prevent movement of the frame in the second direction in the first configuration, and wherein the second blocking member is adapted to allow movement of the frame in the second direction in the second configuration while the cutting roll rotates;
    a third blocking member positioned adjacent the first blocking member, wherein the third blocking member comprises a stop aperture; and a sensor adapted to detect a defective operating configuration and upon sensing the same causing movement of the frame in the second direction.

2. The rotary cutting apparatus of claim 1, wherein the first longitudinal axis and the second longitudinal axis are orthogonal to the first and second directions.

3. The rotary cutting apparatus of claim 1, wherein in the first configuration, the second blocking member is adapted to apply a positive force to the frame in the first direction.

4. The rotary cutting apparatus of claim 1, further comprising a track, wherein the frame is slideably connected with the track.

5. The rotary cutting apparatus of claim 1, wherein the first blocking member is selectively positionable along the first and second directions.

6. The rotary cutting apparatus of claim 1, wherein the second blocking member is selectively positionable along the first and second directions.

7. The rotary cutting apparatus of claim 1, comprising a fourth blocking member positioned adjacent the second blocking member, wherein the fourth blocking member is engageable with a second stop pin.

8. The rotary cutting apparatus of claim 1, comprising a joining member removably connected to the second arm and a portion of the frame.

9. A rotary cutting apparatus having a first mode of operation and a second mode of operation, the rotary cutting apparatus comprising:
   a track having a first side and a second side opposite the first side, wherein the first side and the second side extend in a direction parallel to a machine direction;
   a frame movable in a first direction and a second direction, wherein the first direction is opposite the second direction, wherein the first direction and the second direction are parallel to the machine direction, wherein the frame comprises a first portion extending between the first side of the track and the second side of the track and a second portion extending between the first side of the track and the second side of the track;
   a cutting roll rotatably connected with the frame;
   an anvil roll rotatably connected with the frame;
   a first blocking member located adjacent to the frame and configured to engage the first portion of the frame;
   a second blocking member removeably connected with the second portion of the frame, the secondary blocking member comprising:
      a base;
      a first arm pivotally connected with the base;
      a reciprocating member comprising a first end portion connected to the first arm and a second end portion opposite the first end portion;
      a second arm pivotally connected to the second end portion of the reciprocating member; and
      a joining member connected to the second arm and a portion of the frame; and
   a sensor adapted to detect a defective operating configuration and upon sensing the same causing movement of the frame in the second direction,
   wherein in the first mode of operation, the first blocking member prevents movement of the frame in the first direction and the second blocking member prevents movement of the frame in the second direction,
   wherein in the second mode of operation, the second blocking member allows movement of the frame in the second direction while the cutting roll rotates.

10. The rotary cutting apparatus of claim 9, wherein the frame is moveably connected with the track.

11. The rotary cutting apparatus of claim 9, wherein a transfer apparatus is located adjacent the cutting roll, and wherein a gap is formed between the transfer apparatus and the cutting roll.

12. The rotary cutting apparatus of claim 9, wherein a transfer apparatus is located adjacent the cutting roll, and wherein a gap is formed between the transfer apparatus and the cutting roll.

13. The rotary cutting apparatus of claim 9, comprising a third blocking member positioned adjacent the first blocking member, wherein the third blocking member is engageable with a first stop pin.

14. The rotary cutting apparatus of claim 13, comprising a fourth blocking member positioned adjacent the second blocking member, wherein the fourth blocking member is engageable with a second stop pin.

15. A rotary cutting apparatus comprising:
   a frame movable in a first direction and a second direction, wherein the first direction is opposite the second direction;
   a cutting roll defining a first longitudinal axis, wherein the cutting roll is rotatably connected with the frame and configured to rotate about the first longitudinal axis;
   an anvil roll defining a second longitudinal axis, wherein the anvil roll is rotatably connected with the frame and configured to rotate about the second longitudinal axis, the anvil roll positioned relative to the cutting roll such that the first longitudinal axis is substantially parallel with the second longitudinal axis;
   a first blocking member adapted to prevent movement of the frame in the first direction, wherein the first blocking member is configured to engage a portion of the frame; and
   a second blocking member removably connected with the frame, the second blocking member comprising a base, a first arm connected with the base, a reciprocating member comprising a first end portion connected to the first arm and a second end portion connected to a second arm, wherein the second blocking member comprises first and second configurations, wherein the second blocking member is adapted to prevent movement of the frame in the second direction in the first configuration, wherein the second blocking member is adapted to allow movement of the frame in the second direction in the second configuration, and wherein the cutting roll is configured to rotate while the frame is moved in the second direction;
   a third blocking member positioned adjacent the first blocking member, the third blocking member including a first stop aperture;
   a fourth blocking member positioned adjacent the second blocking member, the fourth blocking member including a second stop aperture; and
   a sensor adapted to detect a defective operating configuration and upon sensing the same causing movement of the frame in the second direction,
   wherein the first longitudinal axis and the second longitudinal axis are orthogonal to the first and second directions.

16. The rotary cutting apparatus of claim 15, wherein in the first configuration, the second blocking member is adapted to apply a positive force to the frame in the first direction.

17. The rotary cutting apparatus of claim 15, further comprising a track, wherein the frame is slideably connected with the track.

18. The rotary cutting apparatus of claim 15, wherein the first blocking member is selectively positionable along the first and second directions.

19. The rotary cutting apparatus of claim 15, comprising a joining member removably connected to the second arm and a portion of the frame.

\* \* \* \* \*